(12) United States Patent
Lam et al.

(10) Patent No.: US 6,582,910 B1
(45) Date of Patent: Jun. 24, 2003

(54) WBPP AND METHOD FOR ASSAY OF WBPP

(76) Inventors: Joseph S. Lam, 2 Bridlewood Drive, Guelph Ontario (CA), N1G 4A6; Carole Creuzenet, 89 Raymond Street, Apt. 401, Guelph Ontario (CA), N1G 3S5

( * ) Notice: Subject to any disclaimer, the term of this patent is extended or adjusted under 35 U.S.C. 154(b) by 0 days.

(21) Appl. No.: 09/580,929

(22) Filed: May 26, 2000

Related U.S. Application Data

(60) Provisional application No. 60/136,564, filed on May 28, 1999.

(51) Int. Cl.$^7$ .................. C07H 21/04; C12N 15/11; C12N 15/85; C12N 15/00; C12Q 1/68
(52) U.S. Cl. .................. 435/6; 435/320.1; 435/69.1; 435/440; 435/325; 435/243; 435/252.3; 536/23.1; 536/23.2; 536/23.7; 536/24.1; 536/24.3; 536/24.32; 536/24.33
(58) Field of Search .................. 435/6, 320.1, 69.1, 435/440, 325, 243, 252.3; 536/23.1, 23.2, 23.7, 24.1, 24.3, 24.32, 24.33

(56) References Cited

U.S. PATENT DOCUMENTS

| | | |
|---|---|---|
| 4,373,071 A | 2/1983 | Itakura |
| 4,401,796 A | 8/1983 | Itakura |
| 4,458,066 A | 7/1984 | Caruthers |
| 4,598,049 A | 7/1986 | Itakura |
| 4,736,866 A | 4/1988 | Leder |
| 4,816,397 A | 3/1989 | Boss |
| 4,816,567 A | 3/1989 | Cabilly |

FOREIGN PATENT DOCUMENTS

| | | |
|---|---|---|
| EP | 0173494 | 11/1987 |
| EP | 171496 | 5/1993 |
| EP | 0239400 | 8/1994 |
| WO | WO92/06193 | 4/1992 |

OTHER PUBLICATIONS

Bauer, A. J., Rayment, I., Frey, P. A., and Holden, H. M. (1992) *Proteins* 12, 372–381.
Belanger, M., Burrows, L.L., and Lam, J.S. (1999) *Microbiology* 145, 3505–3521.
Burrows, L. L., Charter, D. F., and Lam, J. S. (1996) *Mol. Microbiol.* 22, 481–495.
Creuzenet, C., Smith, M., and Lam, J.S. (1999) Pseudomonas'99: biotechnology and pathogenesis. Abstract # 93. Maui, Hawai.
Cryz, S. J., Jr., Pitt, T. L., Furer, E., and Germanier, R. (1984) *Infect. Immun.* 44, 508–513.
Dean, C. R., Franklund, C. V., Retief, J. D., Coyne, M. J., Jr., Hatano, K., Evans, D. J., Pier, G. B., and Goldberg, J. B. (1999) *J. Bacteriol.* 181, 4275–4284.
Engles, W., Endert, J., Kamps, M.A.F., and VanBoven C.P.A. (1985) *Infect. Immun.* 49, 182–189.
Estrela, A. I., Pooley, H. M., de Lencastre, H., and Karamata, D. (1991) *J. Gen. Microbiol.* 137, 943–950.
Flentke, G. R., and Frey, P. A. (1990) *Biochemistry* 29, 2430–2436.
Frey, P. A. (1996) *Faseb J.* 10, 461–470.
Goldberg, J. B., and Pier, G. B. (1996) *Trends Microbiol.* 4, 490–494.
Hancock, R. E., Mutharia, L. M., Chan, L., Darveau, R. P., Speert, D. P., and Pier, G. B. (1983) *Infect. Immun.* 42, 170–277.
Johnson, A. E., and Tanner, M. E. (1998) *Biochemistry* 37, 5746–5754.
Jornvall, H., Persson, B., Krook, M., Atrian, S., Gonzalez–Duarte, R., Jeffery, J., and Ghosh, D. (1995) *Biochemistry* 34, 6003–6013.
Jornvall, H. (1999) *Adv. Exp. Med. Biol.* 463, 359–364.
Jornvall, H., Hoog, J. O., and Persson, B. (1999) *FEBS Lett.* 445, 261–264.
Keppler, O. T., Hinderlich, S., Langner, J., Schwartz–Albiez, R., Reutter, W., and Pawlita, M. (1999) *Science* 284, 1372–1376.
Kiser, K. B., Bhasin, N., Deng, L., and Lee, J. C. (1999) *J. Bacteriol.* 181, 4818–4824.
Knirel, Y. A., Vinogradov, E. V., Shashkov, A. S., Dmitriev, B. A., Kochetkov, N. K., Stanislavsky, E. S., and Mashilova, G. M. (1985) *Eur. J. Biochem.* 150, 541–550.
Knirel, Y. A. (1990) *Crit. Rev. Microbiol.* 17, 273–304.
Knirel, Y. A., and Kochetkov, N. K. (1994) *Biokhimiia* 59, 1325–1383.
Kochetkov, N.K., and Shibaev, V.N. (1973) *Adv. Carbohydr. Chem. Biochem.* 28, 307–399.
Konopka, J. M., Halkides, C. J., Vanhooke, J. L., Gorenstein, D. G., and Frey, P. A. (1989) *Biochemistry* 28, 2645–2654.
Marolda, C. L., and Valvano, M. A. (1995) *J. Bacteriol.* 177, 5539–5546.
Moreno, F., Rodicio, R., and Herrero, P. (1981) *Cell. Mol. Biol.* 27, 589–592.
Morgan, P.M., Sla R.F., and Tanner, M.E. (1997) *J. Am. Chem. Soc.* 119, 10269–10277.
Newton, D. T., and Mangroo, D. (1999) *Biochem. J.* 339, 63–69.
Pier, G.B., and Thomas D.M. (1982) *J. Infect. Dis.* 148, 206–213.
Piller, F., Hanlon, M. H., and Hill, R. L. (1983) *J. Biol. Chem.* 258, 10774–10778.
Pitt, T. L. (1989) *Antibiot. Chemother.* 42, 1–7.

(List continued on next page.)

Primary Examiner—Sean McGarry
(74) Attorney, Agent, or Firm—Bereskin & Parr

(57) ABSTRACT

Novel nucleic acid molecules that are associated with WbpP epimerase which is associated with bacterial infection are disclosed. Proteins encoded by the nucleic acid molecules and antisense oligonucleotides that are complimentary to the nucleic acid molecules are also described. Assays and methods of use of the protein are described.

6 Claims, 12 Drawing Sheets

OTHER PUBLICATIONS

Plumbridge, J., and Vimr, E. (1999) *J. Bacteriol.* 181, 47–54.

Poole, K., Krebes, K., McNally, C., and Neshat, S. (1993) *J. Bacteriol.* 175, 7363–7372.

Poole, K., Gotoh, N., Tsujimoto, H., Zhao, Q., Wada, A., Yamasaki, T., Neshat, S., Yamagishi, J., Li, X. Z., and Nishino, T. (1996) *Mol. Microbiol.* 21, 713–724.

Quimby, B. B., Alano, A., Almashanu, S., DeSandro, A. M., Cowan, T. M., and Fridovich–Keil, J. L. (1997) *Am. J. Hum. Genet.* 61, 590–598.

Reissig, J.L., Strominger J.L., and Leloir, L.F. (1955) *J. Biol. Chem.* 217, 959–966.

Rocchetta, H.L., Burrows, L.L., and Lam, J.S. (1999) *Microbiol. Mol. Biol. Rev.* 63, 523–553.

Rossmann, M. G., and Argos, P. (1975) *J. Biol. Chem.* 250, 7525–7532.

Schiller, N. L., and Hatch, R. A. (1983) *Diagn. Microbiol. Infect. Dis.* 1, 145–157.

Shibaev, V. N. (1986) *Adv. Carbohydr. Chem. Biochem.* 44, 277–339.

Srikumar, R., Tsang, E., and Poole, K. (1999) *J. Antimicrob. Chemother.* 44, 537–540.

Swanson, B. A., and Frey, P. A. (1993) *Biochemistry* 32, 13231–13236.

Thoden, J. B., Frey, P. A., and Holden, H. M. (1996) *Biochemistry* 35, 5137–5144.

Thoden, J. B., Frey, P. A., and Holden, H. M. (1996) *Biochemistry* 35, 2557–2566.

Thoden, J. B., Frey, P. A., and Holden, H. M. (1996) *Protein Sci.* 5, 2149–2161.

Thoden, J. B., Hegeman, A. D., Wesenberg, G., Chapeau, M. C., Frey, P. A., and Holden, H. M. (1997) *Biochemistry* 36, 6294–6304.

Virlogeux, I., Waxin, H., Ecobichon, C., and Popoff, M. Y. (1995) *Microbiology* 141, 3039–3047.

Wilson, D. B., and Hogness, D. S. (1969) *J. Biol. Chem.* 244, 2132–2136.

FIGURE 1

```
*  +++++  +++++         ++*       ******  +++        *        +*       *  *+++++++++
WbpP           MMSRYEELRKELPAQPKVWLITGVAGFIGSNLLETILKLDQKVVGL-DNFATGHQRNLDEVRSLVSEKQWSN-FKFIQGDIRN    81
GalE           MR--VLVTGGSGYIGSHTCVQLLQNGHDVIL-DNL-CNSK-----RSVLPVIERLGGKHPTFVEGDIRN    61
RFFG           MRKILITGGAGFIGSALVRYIINETSDAVVVVDKL-TYA-GNL-MSLAPV--AQ-SERFAFEKVDICD    62
*  +++++ +++++     ***  ******  +**                             *  *  *  ****+  *

***+ +++++++  + *+++++++       ++++++      +        * +++ +   + *+  +    +
---LDDCNNACAGVDYVLHQAALGSVPRSINDPITSNATNIDGFLNMLIAARD-------ARVQSETYAASS-STYGDHPGLPKVEDT-IGK-   161
EALMTEILHDHAIDTVIHFAGLKAVGESVQKPLEYYDNNVNGTLRLISAMRA-------ANVKNFIFSSSA-TVYGDQPKIPYVESFPTGT-   144
RAELARVFTEHQPDCVMHLAAEESHVDRSIDGPAAFIETNIVGTYTLLEAARAYWNALTEDKKSAFRFHHISTDEVYGDLHSTDDFFTETTPYA   155
+ +++ +  * ****  ++         ++*  +     *    *  +  *           +  *     +++

+ ++++ ++   +    * ++ * ++ *++++++        ++          * +      *+ *     * ++   *+++
PLSPYAVTKYVNELYA-DVFSRCYGFSTIGLRYFNVFGRR------QDPNGAYAAVIP--KWTSSMIQGD-DVYIN-GD------GETSRDFC   237
PQSPYGKSKLMVEQILTDLQKAQPDWSIALLRYFNPVGAHPSGDMGEDPQGIPNNLMPYIAQVAV---GRRDSLAIFGNDYPTEDGTGVRDYI   234
PSSPYSASKASSDH-LVRAWLRTYGLPTLITNCSNNYGPYHFPEKL-------IPLMILNALA--GKS-LPV-YGN------GQQIRDWL    227
+ +++  *+     *  * ***  * ** *                   +        *+      *                +++

** * *** ***         +++++++ *** *++   * **      *      *** +++  *+ +++++ * +   *
YIENTVQANLLAATAGLDARNQ-VYNIAVGGRTSLNQLFFALRDGLA------ENGVSYHREPV-YRDFREG-DVRHSLA-DISKAAKLLGYA   320
HVMDLADGHVVAMEKLANKPGVHIYNLGAGVGNSVLDVVNAFSKACG------KPVNYH------FAPRREG-DLPAYWA-DASKADRELNWR   313
YVEDHARALYCVAT--TGK-VGETYNIGGHNERKNLDVVETICELLEELAPNKPHGVAHYRDLITFVADRPGHDLR-Y-AIDASKIARELGCV   315
**  *  *          ** *        **    **    * *                +                ++++++*  *  +

*  **      +        *  * *
PKYDVSAGVALAMPWYIMFLK                                                                          341
VTRTLDEMAQDTWHWQSRHPQGYPD                                                                      338
PQETFESGMRKTVQWYLANESWWKQVQDGSYQGERLGLKG                                                       355
*  **        +            *
```

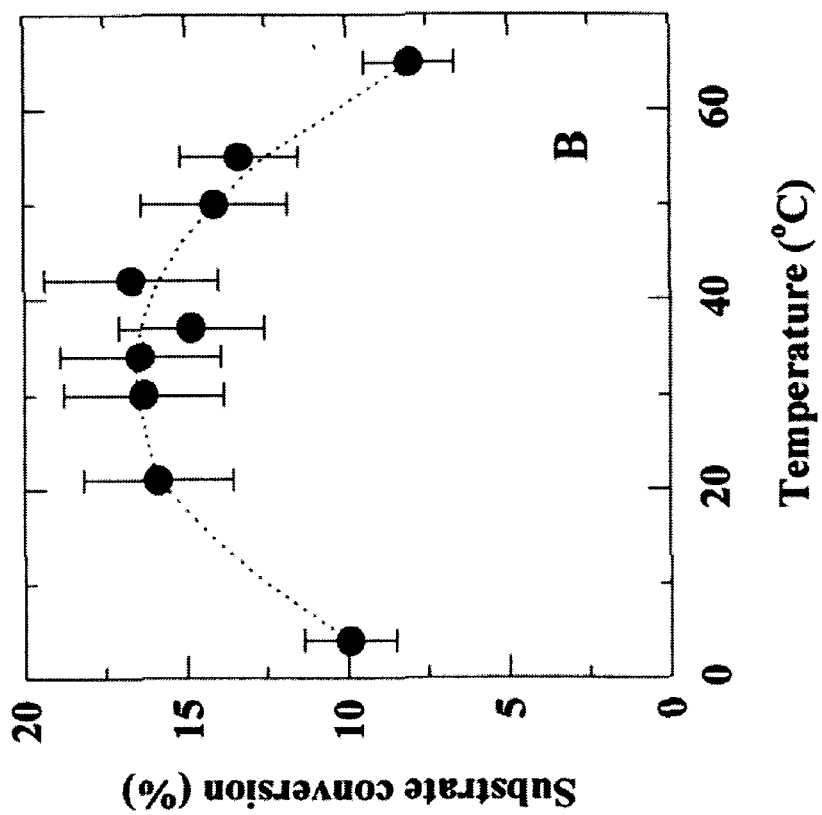
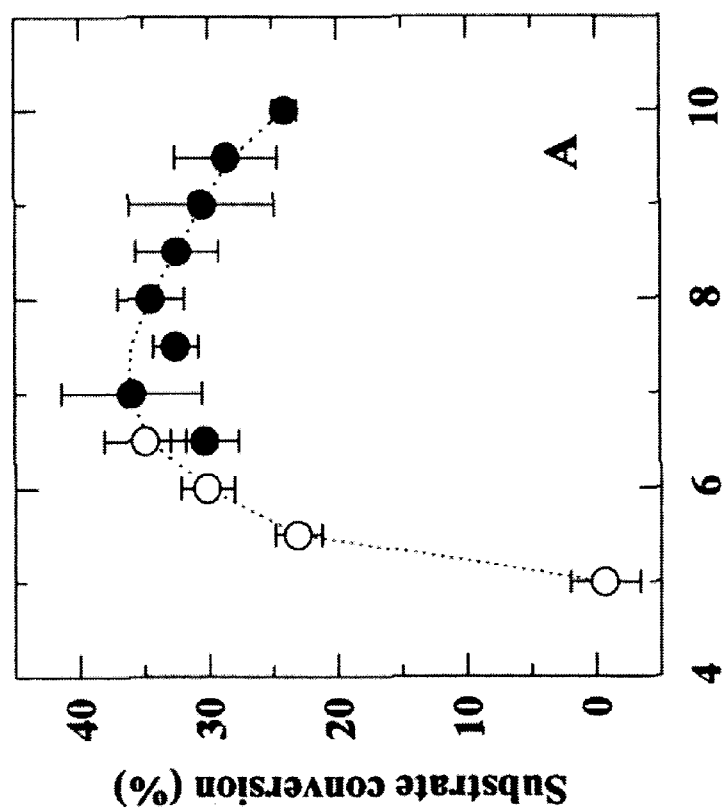
FIGURE 6A
FIGURE 6B

FIGURE 9

```
...1    atgcaccacc  accaccacca  cggttccatg  ggcatgatga  gtcgttatga
..51    agagctaaga  aaggaattgc  cggcgcagcc  gaaagtctgg  ctgattacag
.101    gtgtggcggg  ctttattggc  tctaatcttc  ttgagacttt  gctaaagctt
.151    gatcagaagg  ttgtcggtct  ggataatttt  gctactggtc  atcagcggaa
.201    cctggacgaa  gtgcggtcct  tggttagcga  gaagcaatgg  tcaaatttta
.251    aatttattca  aggtgatatt  cgcaatctgg  atgattgcaa  taacgcctgt
.301    gcaggtgttg  attacgtttt  acatcaagct  gccttgggtt  cggtaccgcg
.351    ttctattaac  gatccgatca  cctccaatgc  aacgaacatc  gatggtttct
.401    tgaatatgct  gattgcagcc  agagatgcca  aggtgcagag  tttcacttat
.451    gcggcaagta  gctctaccta  tggagatcat  cctggtttac  cgaaggtgga
.501    ggatactata  ggtaagcctc  tttcccctta  tgcggttacc  aaatatgtga
.551    atgagcttta  tgccgatgtg  ttttcacgct  gctacggctt  ttcgaccatt
.601    gggcttcgtt  atttcaatgt  gttcggtcgt  cgacaggatc  ccaatggtgc
.651    ctatgcggca  gtcataccaa  aatggacctc  ttcgatgatc  cagggtgatg
.701    acgtctatat  taacggtgat  ggcgagacca  gtcgggattt  tgttatatt
.751    gaaaacaccg  ttcaggccaa  tctgcttgct  gcaaccgcgg  ggcttgatgc
.801    tcgtaatcaa  gtttacaata  ttgctgttgg  cgggcggacg  agtttgaatc
.851    agttgttctt  tgcgcttcgc  gacggccttg  ccgaaaacgg  tgtgtcctat
.901    caccgggaac  ctgtttatcg  tgattttagg  gagggggatg  tacgtcactc
.951    tctcgctgat  atcagcaagg  ctgccaaact  gctggggtat  gcgccgaaat
1001    atgatgtgtc  tgcaggtgtg  gcgttggcca  tgccttggta  catcatgttt
1051    ttgaaatga
```

FIGURE 10

```
  1  MHHHHHHGSM GMMSRYEELR KELPAQPKVW LITGVAGFIG SNLLETLLKL
 51  DQKVVGLDNF ATGHQRNLDE VRSLVSEKQW SNFKFIQGDI RNLDDCNNAC
101  AGVDYVLHQA ALGSVPRSIN DPITSNATNI DGFLNMLIAA RDAKVQSFTY
201  AASSSTYGDH PGLPKVEDTI GKPLSPYAVT KYVNELYADV FSRCYGFSTI
251  GLRYFNVFGR RQDPNGAYAA VIPKWTSSMI QGDDVYINGD GETSRDFCYI
301  ENTVQANLLA ATAGLDARNQ VYNIAVGGRT SLNQLFFALR DGLAENGVSY
351  HREPVYRDFR EGDVRHSLAD ISKAAKLLGY APKYDVSAGV ALAMPWYIMF
     LK
```

WBPP AND METHOD FOR ASSAY OF WBPP

This application claims benefit from United States provisional application serial No. 60/136,564 filed on May 28, 1999.

FIELD OF THE INVENTION

This invention is in the field of bacterial infections and is more particularly concerned with infection by *Pseudomonas aeruginosa* and is specifically concerned with enzymes involved with the synthesis of O antigens, namely WbpP and methods for the use and assay for WbpP.

BACKGROUND OF THE INVENTION

*Pseudomonas aeruginosa* is an opportunistic gram-negative bacterium that can cause life-threatening infections in patients with cystic fibrosis or burn wounds (Hancock et al. (1983)). It produces a wide variety of virulence factors such as proteases, toxins, alginate and lipopolysaccharides (LPS) (Hancock et al. (1983)). Two forms of LPS have been identified: the antigenically conserved A-band LPS, and the variable O-antigen or B-band. B-band LPS is particularly important in the initial steps of the infection, and particularly for evasion of host defenses and colonization (Cryz et al. (1984); Pier et al. (1982)). It contributes to causing initial tissue damage and inflammatory responses in the lungs of patients with cystic fibrosis (Cryz et al. (1984)). *P. aeruginosa* mutants deficient in B-band LPS biosynthesis are more sensitive to serum killing (Hancock et al. (1983); Schiller et al. (1983); Goldberg et al. (1996)) and are more susceptible to phagocytosis (Engles et al (1985)) than wild-type bacteria. They are found almost avirulent in mouse models (Cryz Ct al. (1984)). B-band LPS is the basis for classification of *P. aeruginosa* in 20 different serotypes. Among these, serotypes O6 and O11 are the most clinically relevant in epidemiological studies (Pitt (1989)). To date, the prognosis for a cystic fibrosis patient infected with either serotype of *P. aeruginosa* is rather poor due to intrinsic multidrug resistance of *P. aeruginosa*. Such resistance is due partly to a highly impermeable outer membrane and partly to the presence of multidrug efflux pumps (Poole et al. (1993); Pool et al. (1996); Srikurnar et al. (1999)). Hence, B-band LPS biosynthesis has become an important target for drug discovery.

The genetics of B-band LPS biosynthesis are well documented in serotypes O5, O6 and O11 (Burrows et al. (1996); Belanger et al. (1999); Dean et al. (1999)) and were thoroughly reviewed recently (Rocchetta et al. (1999)). For each of these scrotypes, the entire cluster of genes responsible for B-band LPS synthesis has been sequenced and putative pathways for the synthesis of the corresponding O-antigens have been proposed based on homology studies. In serotype O11, the functional role of these genes awaits further studies. However, in serotypes O5 and O6, extensive functional characterisation has been performed by knockout construction and complementation analysis, using not only genes from *P. aeruginosa* but also homologues found in other organisms. Despite these efforts, ambiguities persist that can only be alleviated by direct biochemical characterisation of the proteins involved. Such a characterisation will also allow screening for inhibitors that might be useful for therapeutic purposes, especially if performed for enzymes found in the clinically relevant serotype 06.

SUMMARY OF THE INVENTION

The present inventors have cloned the nucleic acid sequence of WbpP in an expression vector that allows the production for the first time of large amounts of the WbpP protein.

Accordingly, in one embodiment, the present invention provides an isolated nucleic acid molecule comprising:

(a) a nucleic acid sequence as shown in FIG. 9 (SEQ.ID.NO.:1), wherein T can also be U;

(b) nucleic acid sequences complementary to (a);

(c) nucleic acid sequences which are homologous to (a) or (b);

(d) a fragment of (a) to (c) that is at least 15 bases, preferably 20 to 30 bases, and which will hybridize to (a) to (d) under stringent hybridization conditions, or (e) a nucleic acid molecule differing from any of the nucleic acids of (a) to (c) in cod on sequences due to the degeneracy of the genetic code.

according to another embodiment the present invention provides an isolated nucleic acid molecule having the sequence shown in FIG. 9 (SEQ.ID.NO.:1) (or variants or fragments thereof. The present invention also provides a protein encoded by the nucleic acid sequence of FIG. 9 (SEQ.ID.NO.:1) and shown in FIG. 10 (SEQ.ID.NO.:2). The protein possesses a N-terminal extension as a luistidine tag that allows fast and efficient purification of the enzyme.

Having isolated and purified a WbpP enzyme has allowed the inventors to characterize its function. The O-antigen of B-band LrS of serotype O6 consists of a tetrasaccharide repeat of →-α-D-3 O-acetyl, 6 amino-GalNAcA-(1→4)-α-D-6-amino-GalNFmA-(1→3)-α-D-QuiNAc-(1→2)-α-L-Rha-(1→(15–17). GalNAcA is thought to be synthesized in vivo via epimerisation and dehydrogenation of UP-GIcNAc, the main precursor of surface-associated carbohydrate synthesis (Belanger et al. (1999); Kochetkov et al. (1973); Virlogeux et al. (1995)). The product of the epimerisation reaction, UDP-GalNAc, is an important intermediate for the synthesis of polysaccharide structures that contain GalNAcA or a derivative, not only in *P. aeruginosa* but also in other orgamisms. The gene wbpP is part of the B-band LPS cluster in *P. aeruginosa* O6 (Belanger et al. (1999)). The amino acid sequence of WbpP (FIG. 10 (SEQ ID NO.: 2)) shows 23% identity with the C4 UDP-Glc epimerase GalE from *Escherichia coli*. It also shows 66% identity with WcdB, an enzyme thought to be involved in the formation of GalNAcA residues present in the Vi polysaccharide of *Salmonella typhi* (Virlogeux et al. (1995)). Disruption of the wbpP gene in a knockout mutant results in loss of B-band LPS production in *P. aeruginosa* and, this deficiency is fully alleviated after complementation by the wcdB homologue (Belanger et al. (1999)). Though no biochemical evidence is available for either WbpP or WcdB, sequence comparisons with other proteins and carbohydrate composition analysis suggest that they are C4 epimerases that transform UDP-GlcNAc into UDP-GalNAc in vivo.

A functional assignment relying mainly on homology studies is particularly problematic in the case of putative epimerases. Epimerases belong to the short-chain dehydrogenase/reductase (SDR) enzyme family. This family includes enzymes responsible for a wide variety of functions (Jornval et al. (1995); Jornvall (*Adv. Exp. Med. Biol.* 463, 359–364 (1999)); Jornvall et al. (PEBS Lett. 445, 261–264 (1999)). Most of these enzymes possess common features which include the presence of the G-x-x-G-x-x-G signature for nucleotide binding proteins and the presence of alternating α and β structures which delineate a typical nucleotide binding Rossman fold at their N-terminus (Rossmann, et al. (1975); Bauer et al. (1992)). Moreover, they share a conserved catalytic triad $S-(x)_{24}-Y-(x)_{3}3-K$ probably involved in initiation of the catalytic process. All these features arc present in WbpP and they match perfectly with those found in the C4 UDP-Gal epimerase GalE found in *E. coli* (FIG. 1) but also those of other enzymes with different functions such as RFPG, a dTDP-glucose 4,6-dehydratase present in *E. coli* (Marolda et al. (1995)). Here is described the work conducted by the inventors to perform the biochemical analysis necessary to prove without ambiguity the function of WbpP, namely, that of a C4 UDP-GlcNAc epimerase. This describes the first epimerase for the N-acetylated form of the substrate.

The present invention also includes expression vectors containing the nucleic acid molecules of the present invention. The expression vectors will contain the necessary regulatory regions to provide for expression of the histidine tagged protein.

The present invention further provides host cells which have been transformed with the expression vectors of the present invention.

Accordingly, the present invention provides a method for expressing a protein having WbpP comprising inserting a nucleic acid molecule encoding the protein into an appropriate expression vector; transforming a host cell with the expression vector; and providing conditions which allow for expression of the protein. Preferably the protein is expressed in soluble and active form.

In another embodiment the present invention provides a method of assaying for WbpP activity in a sample comprising adding a sufficient amount of UDP GalNAc to the sample, under appropriate conditions for reaction, and assaying for UDP GlcNAc, wherein the appearance of UDP GlcNAc reflects the presence of WbpP activity. Preferably the amount of UDP GlcNAc which appears is determined, and preferably the amount of UDP GlcNAc which is determined is correlated to the amount of the substance providing the WbpP activity in order to determine the amount of the substance providing the WbpP activity which is in the sample. Preferably the amount of UDP-GlcNAc formed is determined by spectropholometric assay using p-dimethylaminobenzaldehyde (DMAB).

According to another embodiment, the present invention provides a method of assaying for WbpP activity in a sample comprising adding a sufficient amount of UDP GlcNAc to the sample, under appropriate conditions for reaction, and assaying for changes in the presence of UDP GlcNAc, wherein a disappearance, or reduction in UDP GlcNAc reflects the presence of WbpP activity. Preferably changes in the amount of UDP GlcNAc are determined and preferably the amount of UDP-GlcNAc which is determined is correlated to the amount of the substance providing the WbpP activity in order to determine the amount of the substance providing the WbpP activity which is in the sample. Preferably the amount of UDP-GlcNAc is determined by spectrophotometric assay using p-dimethylaminobenzaldeliyde (DMAB).

In another aspect, the present invention provides an assay for detecting inhibitors of a substance with WbpP activity. Accordingly, the present invention further provides a method for screening for an inhibitor of a substance with WbpP activity comprising (a) incubating a test sample containing (i) an substance with WbpP activity, (ii) a substance suspected of being an inhibitor of the substance; and (iii) UDP-GlcNAc or UDP-GalNAc; (b) stopping the reaction; (c) comparing the amount of UDP-GlcNAc, or UDP-GalNAc in the test sample with the amount in a control sample (that does not contain the substance suspected of being an inhibitor) wherein a decrease in the amount of GlcNAc, or UDP-GalNAc in the control sample as compared to the test sample indicates that the substance is an inhibitor of the substance with WbpP activity.

The present invention further provides a method for diagnosing or detecting an infection, preferably those associated with *Pseudomonas aeruginosa,* comprising detecting the presence of a nucleic acid or protein of the present invention in a biological sample.

The present invention also provides a method for inhibiting infection of an animal, preferably those infections associated with *Pseudomonas aeruginosa,* comprising inhibiting the transcription or translation (i.e., expression) of a nucleic acid molecule of the present invention. The expression of the nucleic acid molecule may be inhibited using antisense oligonucleotides that are complimentary to the nucleic acid molecules of the invention.

The present invention further provides a method for inhibiting infection in an animal comprising inhibiting the activity of the proteins of the present invention. The proteins of the present invention may be inhibited by using an antibody that is specific for the protein.

According, to another aspect, the present invention provides a method for converting UDP-GlcNAc to UDP-GalNAc. UDP-N-acetylgalactosamine (UDPGalNAc) may be used as a substrate in an assay. UDP-GalNAc is very expensive. Consequently, the inventors have developed a method of producing UDPGalNAc from UDP-N-acetylglucosamine (UDPGlcNAc) which is less costly: Namely the present invention provides a method of producing UDPGalNAc comprising incubating an epimerase in the presence of UDPGlcNAc under appropriate conditions for the production of UDPGalNAc. Preferably, the epimerase is WbpP from serotype O6 (WbpPO6). Preferably the amount of UDP-GalNAc formed is determined by spectrophotometric assay using p-dimethylaminobenzaldehyde (DMAB).

The present invention also provides a method of inhibiting the epimerization of UDP-GalNAc. Preferably inhibition may be achieved through inhibition of expression of the nucleic acid molecule using antisense oligonucleotides that are complimentary to the nucleic acid molecules of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

FIG. 1 illustrates a comparison of the primary and secondary structural features of 3 members of the short-chain dehydrogenase/reductase family including WbpP (SEQ.ID.NOS:3, 4, and 5).

FIG. 6A is a graph illustrating the relationship between pH and epimerisation of UDP-GlcNAc by WbpP using the DMAB assay.

FIG. 6B is a graph illustrating the relationship between temperature and epimerisation of UDP-GlcNAc by WbpP using the DMAB assay.

FIG. 9 is the DNA sequence of WbpPO6 carrying a N-terminal hexahistidine tag (in bold).

FIG. 10 is the amino acid sequence of WbpPO6 carrying a N-terminal hexahistidine tag (in bold).

DETAILED DESCRIPTION OF THE INVENTION

Figure 2:
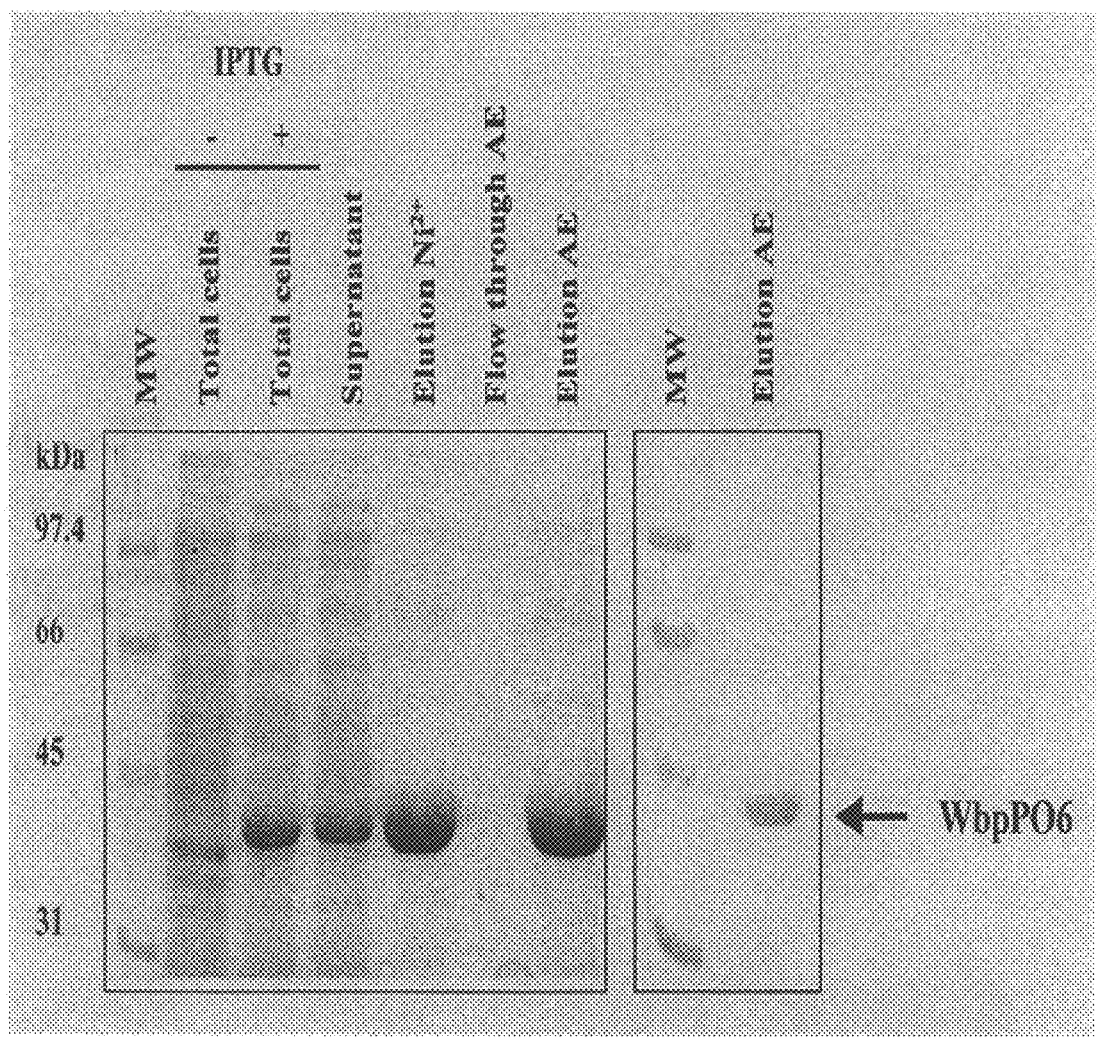
FIG. 2 shows an SDS-PAGE analysis of WbpP through steps of its purification.

As mentioned above, the present inventors have isolated and purified the nucleic acid sequence of WbpP, and deduced the amino acid sequence of the enzyme. Further, the authors have cloned the nucleic acid sequence of WbpP in an expression vector and have expressed the protein in an active form and determined its functional activity all of which will now be described in further detail. It is understood by those skilled in the art that the term "expression of the protein" includes expression and overexpression.

As used herein "WbpP activity" means an epimerase activity of a substance including conversion of UDP-GalNAc to UDP-GlcNAc and vice versa.

As used herein "appropriate conditions" means those conditions, as understood by those skilled in the art, including temperature, time, volumes and quantities of reactants, pressure which allow for reactants to undergo a reaction to give reaction products.

As used herein "sufficient amount" means an amount of a substance or reactant to result in an observable reaction product.

The term "animal" as used herein includes all members of the animal kingdom including mammals, preferably humans.

As used herein, the following symbols have the following meaning: LPS, lipopolysaccharide; UDP, uridyl diphospho nucleoside; Glc, glucose; Gal, galactose; GlcNAc, N-acetyl glucosamnine; GalNAc, N-acetyl galactosamine; DMAB, p-dimethylaminobenzaldehyde; SDR, short-chain dehydrogenase/reductase; CE, capillary electrophoresis; PAGE, polyacrylamide gel electrophoresis, IPTG, isopropyl-1-thio-β-D-galactopyranoside; IMAC: immobilized metal affinity chromatography.

I. Nucleic Acid Molecules of the Invention

As just stated the present invention relates to isolated nucleic acid molecules of WbpP and the cloning of the nucleic acid sequence of WbpP in an expression vector and expression the protein in an active form. The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

In an embodiment of the invention, an isolated nucleic acid molecule is provided having a sequence as shown in FIG. 9 (SEQ.ID.NO.:1), or a fragment or variant thereof.

Preferably, the isolated nucleic acid molecule comprises (a)-a nucleic acid sequence as shown in FIG. 9 (SEQ.ID.NO.:1), wherein T can also be U; (b) nucleic acid sequences complementary to (a); (c) nucleic acid sequences which are homologous to (a) or (b); (d) a fragment of (a) to (c) that is at least 15 bases, preferably 20 to 30 bases, and which will hybridize to (a) to (d) under stringent hybridization conditions; or (e) a nucleic acid molecule differing from any of the nucleic acids of (a) to (c) in codon sequences due to the degeneracy of the genetic code.

It will be appreciated that the invention includes nucleic acid molecules encoding truncations of the proteins of the invention, and analogs and homologs of the proteins of the invention and truncations thereof, as described below. It will further be appreciated that variant forms of the nucleic acid molecules of the invention which arise by alternative splicing of an mRNA corresponding to a cDNA of the invention are encompassed by the invention.

Further, it will be appreciated that the invention includes nucleic acid molecules comprising nucleic acid sequences having substantial sequence homology with the nucleic acid sequence as shown in SEQ.ID.NO.:1 and fragments thereof. The term "sequences having substantial sequence homology" means those nucleic acid sequences which have slight or inconsequential sequence variations from these sequences, i. e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80–90% identity with the nucleic acid sequence as shown in FIG. 9 (SEQ ID. NO.: 1).

Another aspect of the invention provides a nucleic acid molecule, and fragments thereof having at least 15 bases, which hybridizes to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 2.0×SSC at 50° C. In addition, the temperature in the wash step can be at high stringency conditions, at about 65° C.

Isolated and purified nucleic acid molecules having sequences which differ from the nucleic acid sequence shown in FIG. 9 (SEQ ID. NO.: 1) due to degeneracy in the genetic code are also within the scope of the invention.

Nucleic acid molecules of the invention can be isolated by preparing a labelled nucleic acid probe based on all or part of the nucleic acid sequence as shown in FIG. 9 (SEQ ID. NO.: 1), and using this labelled nucleic acid probe to screen an appropriate DNA library (e.g. a cDNA or genomic DNA library). For example, a human and mouse libraries can be used to isolate a DNA encoding a novel protein of the invention by screening the library with the labelled probe using standard techniques. Nucleic acids isolated by screening of a cDNA or genomic DNA library can be sequenced by standard techniques.

Nucleic acid molecules of the invention can also be isolated by selectively amplifying a nucleic acid using the polymerase chain reaction (PCR) method and cDNA or genomic DNA. It is possible to design synthetic oligonucleotide primers from the nucleic acid molecules as shown in FIG. 9 (SEQ ID. NO.: 1) for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a protein of the invention.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in the Sequence Listing as SEQ.ID.NO.1 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with MRNA or the native gene e.g., phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further broadly contemplates an isolated protein encoded by the nucleic acid molecules of the invention. Within the context of the present invention, a protein of the invention may include various structural forms of the primary protein which retain biological activity.

In an embodiment the protein has the amino acid sequence shown in FIG. 10 (SEQ.ID.NO.:2).

In addition to full length amino acid sequences the proteins of the present invention also include truncations of the protein, and analogs, and homologs of the protein and truncations thereof as described herein. Truncated proteins may comprise peptides of at least fifteen amino acid residues.

The truncated proteins may have an amino group (NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end.

Analogs of the protein having the amino acid sequence shown in SEQ.ID.NO.:2 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characterisitics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequence shown in SEQ.ID.NO.:2. Amino acid insertions may consist of single amino acid residues or sequential amino acids ranging from 2 to 15 amino acids in length. For example, amino acid insertions may be used to destroy target sequences so that the protein is no longer active. This procedure may be used in vivao to inhibit the activity of a protein of the invention. Alternatively, mutatins could be introduced that will increase the yield of production of UDP-GalNAc from UDP-GlcNAc (and vice versa) in vitro.

Deletions may consist of the removal of one or more amino acids, or discrete portions from the amino acid sequence shown in SEQ.ID.NO.:2. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonuclcotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence shown in SEQ.ID.NO.:2 and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention.

A homologous protein includes a protein with an amino acid sequence having at least 70%, preferably 80–90% identity with the amino acid sequence as shown in SEQ.ID.NO.:2.

The invention also contemplates isoforms of the protein of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and reglatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiationr signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector. That is, the DNA molecule is operatively linked to a regulatory sequence in a manner which allows for expression, by transcription of the DNA molecule, of an RNA molecule and subsequent translation into a protein corresponding to WbpP.

The recombinant expression vectors of the invention may also contain a selectable marker gene which facilitates the selection of host cells transformed or transfected with a recombinant molecule of the invention. Examples of selectable marker genes are genes encoding a protein such as G418, ampicilin, and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nudeic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification, For example, a proteolytic cleavage site may be added to the target recombinant protein to allow separation of the recombinant protein from the fusion moiety subsequent to purification of the fusion protein.

Recombinant expression vectors can be introduced into host cells to produce a transformant host cell. The term "transformant host cell" is intended to include prokaryotic and eukaryotic cells whicl have been transformed or transfected with a recombinant expression vector of the invention. The terms "transformed with", "transfected with", "transformation" and "transfection" arc intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcum chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Fxprcssion Technology: Methods in Enzymology 185, Academic Press, San Diego, Calif. (1991).

A host cell may also be chosen which modulates the expression of an inserted nucleic acid sequence, or modifies (e.g. glycosylation or phosphorylation) and processes (e.g. cleaves) the protein in a desired fashion. Host systems or cell lines may be selected which have specific and characteristic mechanisms for post-translational processing and modification of proteins. For example, eukaryotic host cells including CHO, VERO, BHK, HeLA, COS, MDCK, 293, 3T3, and WI38 may be used. For long-term high-yield stable expression of the protein, cell lines and host systems which stably express the gene product may be engineered. Host cells and in particular cell lines produced using the methods described herein may be particularly useful in screening and evaluating compounds that mnodulate the activity of a protein of the invention.

The proteins of the invention may also be expressed in non-human transgenic animnals including but not limited to mice, rats, rabbits, guinea pigs, micro-pigs, goats, sheep, pigs, non-human primates (e.g. baboons, monkeys, and chimpanzees) (see Hammer et al. (Nature 315:680–683, 1985), Palmiter et al. (Science 222:809–814, 1983), Brinster et al. (Proc. Natl. Acad. Sci USA 82:4438–4442, 1985), Palmiter and Brinster (Cell. 41:343–345, 1985) and U.S. Pat. No. 4,736,866). Procedures known in the art may be used to introduce a nucleic acid molecule of the invention into animals to produce the founder lines of transgenic animals. Such procedures include pronuclear microinjection, retrovirus mediated gene transfer into germ lines, gene targeting in embryonic stem cells, electroporation of embryos, and sperm-mediated gene transfer.

The present invention contemplates a transgenic animal that carries a nucleic acid of the invention in all their cells, and animals which carry the transgene in some but not all their cells. The transgene may be integrated as a single transgene or in concatamers. The transgene may be selectively introduced into and activated in specific cell types (See for example, Lasko et al, 1992 Proc. Natl. Acad. Sci. USA 89:6236). The transgene may be integrated into the chromosomal site of the endogenous gene by gene targeting. The transgene may be selectively introduced into a particular cell type inactivating the endogenous gene in that cell type (See Cu et al., Science 265:103–106).

The expression of a recombinant protein of the invention in a transgenic animal may be assayed using standard techniques. Initial screening may be conducted by Southern Blot analysis, or PCR methods to analyze whether the transgene has been integrated. The level of mRNA expression in the tissues of transgenic animals may also be assessed using techniques including Northern blot analysis of tissue samples, in situ hybridization, and RT-PCR. Tissue may also be evaluated immunocytochemically using antibodies against a protein of the invention.

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of organic Chemistry, ed. E. Wansch, Vol. 15 I and II, Thieme, Stuttgart).

N-terminal or C-terminal fusion proteins comprising a protein of the invention conjugated with other molecules, such as proteins may be prepared by fusing, through recombinant techniques, the N-terminal or C-terminal of the protein, and the sequence of a selected protein or marker protein with a desired biological function. The resultant fusion proteins contain a protein of the invention fused to the selected protein or marker protein as described herein. Examples of proteins which may be used to prepare fusion proteins include imnunoglobulins, glutathione-S-transferase (GST), hemagglutinin (HA), and truncated myc.

III. Applications

Methods of Modulating Epimerase Function

The present invention further relates to methods of modulating the epimerase function of WbpP. In *Pseudomonas aeruginosa* this epimerase activity converts UDP-GlcNAc to UDP-GalNAc. Because WbpP is able to epimerize UDP-GlcNAc to UDP-GalNAc this function can be used to commercially convert UDP-GlcNAc to UDP GalNAc. In another embodiment the invention provides a method for assaying for WbpP activity comprising adding a sufficient amount of UDP-GlcNAc to a sample, allowing sufficient time under appropriate conditions for reaction and assaying for the disappearance of UDP-GlcNAc. In yet another embodiment the invention provides a method for assaying for WbpP activity comprising adding a sufficient amount of UDP-GlcNAc to a sample, allowing sufficient time under appropriate conditions for reaction and assaying for the amount of disappearance of UDP-GlcNAc and correlating the amount of UDP-GalNAc formed with the amount of WbpP.

The present invention also provides an assay for detecting inhibitors of a substance with WbpP activity. The method for screening for an inhibitor of a substance with WbpP activity comprises (a) incubating a test sample containing (i) an substance with WbpP activity, (ii) a substance suspected of being an inhibitor of the substance; and (iii) UDP-GlcNAc or UDP-GalNAc; (b) stopping the reaction; (c) comparing the amount of UDP-GlcNAc, or UDP-GalNAc in the test sample with the amount in a control sample (that does not contain the substance suspected of being an inhibitor) wherein a decrease in the amount of GlcNAc, or UDP-GalNAc in the control sample as compared to the test sample indicates that the substance is an inhibitor of the substance with WbpP activity.

Therapeutic Applications
Antisense and Antibodies

The present invention further provides a method of treating a bacterial infection by inhibiting the expression of a nucleic acid molecule of the present invention or by inhibiting the activity of a protein of the invention. In one embodiment, the nucleic acids of the invention encode a WbpP protein which is associated with B band LPS synthesis. Accordingly, the present invention also provides a method for controlling bacterial infections by inhibiting the expression of a nucleic acid or protein of the invention. The expression of the nucleic acid molecule may be inhibited using antisense oligonucleotides as described below.

Antisense Oligonucleotides

The sequence of a nucleic acid molecule of the invention may be inverted relative to its normal presentation for transcription to produce an antisense nucleic acid molecule. Preferably, an antisense sequence is constructed by inverting a region preceding the initiation codon or an unobserved region. In particular, the nucleic acid sequence contained in the nucleic acid molecule of the invention or a fragment thereof, preferably a nucleic acid sequence shown in the Sequence Listing as SEQ.ID.NOS.:1 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotide as shown in SEQ.ID.NO.:1. Regulatory sequences operatively linked to the antisense nucleic acid can be chosen which direct the continuous expression of the antisense RNA molecule.

The activity of the proteins of the present invention may be inhibited by using an antibodies that are specific for the proteins of the invention as described in detail above. Conventional methods can be used to prepare the antibodies. For example, by using a peptide or a protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256,495–497 (1975)) as well as other techniques such as the human B-cell hybridoma technique (Kozbor et al., Immunol. Today 4, 72 (1983)), the EBV-hybridoma technique to produce human monoclonal antibodies (Cole et al., Monoclonal Antibodies in Cancer Therapy (1985) Allen R. Bliss, Inc., pages 77–96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein, of the invention, or peptide thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a protein of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain).

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

Compositions

The antisense oligonucleotides and antibodies may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Recombinant molecules comprising an antisense sequence or oligonucleotide fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

Vaccines

The present invention also relates to a method of preventing or treating a bacterial infection by *Pseudomonas aeruginosa* by administering a vaccine that will induce an immune response against the protein of the invention.

The vaccine can be a nucleic acid vaccine or a protein based vaccine containing a nucleic acid or protein of the invention, respectively. A nucleic acid vaccine will contain the nucleic acid sequence in a vector suitable for expression of the protein in the host.

The vaccine may comprise an immunologically acceptable carrier such as aqueous diluents, suspending aids, buffers, excipients, and one or more adjuvants known in the art. The vaccine may also contain preservatives such as sodium azide, thimersol, beta propiolactone, and binary ethyleneiinine.

The vaccines of the invention can be intended for administration to animals, including mammals, avian species, and fish; preferably humans and various other mammals, including bovines, equines, and swine. The vaccines of the invention may be administered in a convenient manner, such as intravenously, intramuscularly, subcutaneously, intraperitoneally, intranasally or orally. The dosage will depend on the desired effect and on the chosen route of administration, and other factors known to persons skilled in the art.

Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

The following non-limiting examples are illustrative of the present invention:

EXAMPLES

Materials and Methods for Examples

Materials—Unless stated otherwise all chemical reagents used were from Sigma (St Louis, Mo.). Restriction enzymes and T4 DNA ligase were from Gibco/BRL (Gaitherburg, Md.). Pwo DNA polymerase was from Boehringer-Mannheim (Laval, Quebec). The dNTPs were from Perkin Elmer (Markharn, ON). The pentaHis anti-histidine tag antibody was from Qiagen (Santa Clarita, Calif.). Agar was from Difco (Detroit, Mich.). All kits or enzymes were used following the manufacturer's instructions.

Cloning and overexpression of WbpP in the pET system—WbpP was cloned in the NcoI and LcoRI sites of a pET23 derivative (26) with a N-terminal hitidine tag. The sequence of the primers used to amplify wbpP by PCR from genomic DNA (strain LATS O6) were (SEQ.ID.NO.6) and (SEQ.ID.NO.7) for the top and bottom primers, respectively. The PCR reaction consisted 100 ng of genomic DNA, 0.5 µM each primer, 0.2 mM each dNTP, 4 mM MgC12 and 1×buffer in a total of 50 µl. A 5 min denaturation at 94° C. was done before addition of DNA polymerase (1.5 units of Pwo). This was followed by 15 cycles of 1 min at 94° C., 45 sec at 55° C. and 90 sec at 72° C. A final 7 min elongation was performed at 72° C. The constructs obtained were checked by restriction analysis and sequencing.

The construct was subsequently transformed into the expression strain BL21(DE3)pLysS (Novagen, Madison, Wis.) with ampicillin (100 µg/ml) and chloramphenicol (35 µg/ml) selection. For protein expression, 2 ml of an overnight culture were inoculated into 100 ml of LB in the presence of ampicillin and chloramphenicol. The culture was grown at 30° C. When the $OD_{600\ nm}$ reached 0.6, JPTC (Promega, Madison, Wis.) was added to a final concentration of 0.15 mM and expression was allowed to proceed for 5 to 6 h at 30° C. Cells were harvested by centrifugation at 5,000 g for 15 min at 4° C. and the pellet was stored at −20° C. until needed. Lxpression was monitored by SDS-PAGE analysis, with Coomassie blue staining or Western immunoblot using the penta-His anti-histidine tag antibody as instructed by the manufacturer.

Purification of WbpP by chromatography—Cells sedimented from 100 ml induced culture were resuspended in 10 ml of buffer A (5 mM imidazole, 20 mM Tris pH 8, 0.1 M NaCl). The cells were briefly sonicated (macrotip, sonicator XL2020 Heat systems Incorporated, power set to 4, 2 min total, 5 sec on, 5 sec off) on ice. Cell debris were removed by centrifugation at 13000×g for 15 min at 4° C. and the supernatant was applied to a 3 ml fast flow cielating sepharose column (Amersham-Pharmacia, Quebec) previously loaded with nickel sulfate (30 ml of 0.1 M) and equilibrated with 5 column volumes (CV) of buffer A. Loading of the sample as well as all washing and elution steps were done by gravity. After loading of the sample, the column was washed with 10 CV of buffer A and 5 CV of buffer B (20 mM imidazole, 20 mM Tris pH 8, 0.1M NaCl). Elution was carried out with 3 CV of buffer C (1 M imidazole, 20 mM Tris pH 8, 0.5 M NaCl 0.1 M). Fractions were collected every 1 CV. Most of the protein was eluted in fraction number 2 as seen by SDS-PAGE analysis. This fraction was subjected to further purification by anion exchange chromatography after dilution 1/30 in 50 mM Tris pH 8. Half of it was loaded onto a 1 ml column of Q Sepharose fast flow (Pharmacia). The column was washed with 30 CV of Tris buffer and the protein was eluted with 3 CV of 50 mM Tris pH 8, 0.5 M NaCl. Fractions were collected every 1 CV and most of the protein was recovered in fraction 2. This fraction was desalted by overnight dialysis (cut off 3500 Da) in 50 mM Tris pH 8 at 40° C. The dialysed samples were concentrated by overlay with PEG 8000 (Sigma) for 2 to 3 h at 4° C. Protein quantitation was done using the BCA reagent (Pierce, Rockford, Ill.). The purified enzyme was either used fresh or stored at −20° C. in 25% glycerol or 20% adonitol in 50 mM Tris, pH 8 without any significant loss of activity.

Determination of the oligomerisation status by gel filtration analysis—A 45×1.6 cm column containing 90 ml of G100 Sephadex (Sigma, fractionation range 4–150 kDa) was used to determine the oligomerisation status of WbpP. The column was equilibrated in 50 mM Tris pH 8 containing 100 mM NaCl and run at 1.4 ml/min. Molecular weight standards (Sigma, 12–150 kDa) were applied onto the column one by one (50–200 µg each in 200 µl). WbpP was applied onto the column either as a concentrated or a diluted solution (200 µg or 50 µg/200 µl deposited). Protein elution was monitored at 280 nm.

Extraction of NAD(H) from purfied WbpP—A freshly purified and extensively dialysed sample of WbpP at 1.75 mg/ml in 50 mM Tris pH 8 was used for the extraction and quantification of bound NAD(H). WbpP (175 µg) was incubated in the presence of 10 µg of proteinase K for 45 min at 37° C. Total digestion of WbpP was checked by SDS-PAGE analysis and Coomassie staining. After complete digestion, WbpP was submitted to chemical reduction by successive additions of 1 µl of 10 mg/ml of sodium borohydride (Fisher, Nepean, ON) every 30 min for 2 h 30 min. The proteolysis step was included prior to reduction to ensure quantitative reduction and recovery of NAD(H). The absorption spectrum was recorded before and after chemical reduction between 230 and 450 nm using a DU520 spectrophotometer (Beckman Fullerton, Calif.) equipped with a 50 µl microcell. Serial dilutions of NAD+ (Sigma) ranging from 5 to 40 µM were prepared in 50 mM Tris pH 8 and were incubated at 37° C. for the same amount of time as WbpP with or without chemical reduction. The precise concentration in NAD+ was calculated using $\epsilon_{260\ nm}=17400\ M^{-1} \times cm^{-1}$ and the efficiency of reduction was calculated using $\epsilon_{340\ nm}=6270\ M{-}1 \times cm^{-1}$.

Determination of the enzymatic conversion of UDP-GlcNAc and UDP-GalNAc using p-dimethylaminobenzaldehyde (DMAB)—Reactions were performed with a total reaction volume of 35 µl at 37° C. in 20 mM Tris pH 8 unless stated otherwise. The specific amount of enzyme used, substrate concentrations, and incubation time are indicated in the legend of each figure. The reactions were stopped by acid hydrolysis of the UDP moiety of the substrate. For this purpose, the samples were acidified to pH 2 by addition of 7 µl of HCl 0.1 N, boiled for 6 min, and neutralised by addition of 7 µl of NaOH 0.1 N. For the spectrophotometric quantification of GalNAc and GlcNAc, the reagent DMAB was prepared at 10% in glacial acetic acid/HCl 9/1 v/v, and further diluted 1/10 in glacial acetic acid before use (Reissig et al. (1955)). For the assay itself, 100 µl of 0.2 M sodium tetraborate pH 9.1 were added to 50 µl of quenched and neutralised enzymatic reactions and boiled immediately for 3 min. 40 µl of this mixture were transferred to a microtitration plate and 200 µl of DMAB reagent were added. After incubation for 30 min at 37° C., the OD595 nm was recorded using a microplate reader. For practical reasons, the DMAB assay was carried out using a wavelength setting of 595 nm in the spectrophotometer. However, the signal of the assay could be increased by ca. 15% if the wavelength is adjusted to 580 nm. The assay was done in duplicate for each reaction tested. Standard curves were prepared using UDP-GlcNAc and UDP-GalNAc that were subjected to acid hydrolysis in the same conditions as described above.

Determination of the kinetic parameters for UDP-GlcNAc and UDP-GalNAc by capillary electrophoresis—Reactions were performed at 37° C. in 20 mM Tris pH 8 with a total reaction volume of 44 µl. The amount of purified enzyme added was 234 ng and 117 ng for reaction with UDP-GlcNAc and UDP-GalNAc, respectively. After incubation at 37° C. for the required amount of time, the reactions were quenched by boiling the sample for 6 min. Time course studies were performed with final sugar-nucleotide concentrations of 0.075 and 1.75 mM. Samples were quenched after 0, 2, 4, 6, 8, 10 and 15 min. For Km and Vmax determinations, the final sugar nucleotide concentrations ranged from 0.075 to 1.75 mM and the reactions were quenched after 3 min of incubation. Capillary electrophoresis (CE) analysis was performed using a P/ACE 5000 system (Beckman, Fullerton, Calif.) with UV detection. The running buffer was 25 mM sodium tetraborate pH 9.4. The capillary was bare silica 75 µm×57 cm, with a detector at 50 cm. The capillary was conditioned before each run by washing with 0.2 M NaOH for 2 min, water for 2 min, and running buffer for 2 min. Samples were introduced by pressure injection for 4 s and the separation was performed at 22 kV. Peak integration was done using the Beckman P/ACE Station software. The calculation of kinetic parameters was done using the PRISM program.

Study of the Requirement for NAD+ or divalent cations for enzymatic activity—To access the requirement for NAD+ or divalent cations for the enzymatic activity of WbpP, reactions were carried out with or without NAD+ (1 mM final concentration), and with or without divalent cations (4 mM final concentration of $MnCl_2$, $MgCl_2$, or $CaCl_2$) and monitored by capillary electrophoresis as described above.

Spectrophotometric study of the epimerisation of UDP-Glc and UDP-Gal by WbpP—The enzymatic reactions were performed in 20 mM Tris pH 8, with 39 µg of freshly purified enzyme and 0.8 mM sugar-nucleotide in a total reaction volume of 44 µl. Time course studies were performed over 2 hours at 37° C. After incubation for the required amount of time, the reactions were quenched by acid hydrolysis of the UDP moiety as described above. Standard curves were prepared using UDP-Glc or UDP-Gal that were also subjected to acid hydrolysis. The quantitation of remaining glucose present in the reaction mixture was measured spectrophotometrically using a coupled assay adapted from Moreno et al. (Moreno et al. (1981)), A reaction mix containing 22 units/ml of glucose oxidase, 7 units/ml of horse radish peroxidase and 0.3 mg/ml of O-dianisidine was prepared in 50 mM sodium acetate buffer, pH 5.5. Four hundred µl of this reaction mix were added to the neutralised samples described above and the reaction was allowed to proceed for 30 min at 37° C. The reaction was then quenched by addition of 600 µl of 6 N HCl and the optical density at 540 nm was read.

Determination of the kinetic parameters for UDP-Glc and UDP-Gal by capillary electrophoreis—The enzymatic reactions were performed in 20 mM Tris pH 8, with 16.4 µg of freshly purified enzyme in a total reaction volume of 44.8 µl. The total sugar nucleotide concentrations in the enzymatic reactions ranged from 0.048 to 2.009 mM. The reactions were quenched after 15 min of incubation at 37° C. The samples were analysed by CE in the same conditions as described above and the Km and Vmax values were determined using the PRISM software.

Example 1

Protein expression and purification—WbpP is a 37.7 kDa protein with a slightly acidic isoelectric point (pI=5.99). It was expressed in the pET system as a N-terminally histidine-tagged protein. Provided that expression was carried out at low temperature (30° C.) and with a low concentration of inducer IPTG (0.15 mM), most of the protein was expressed in a soluble form (FIG. 2). It was expressed at a very high level since it represented 30–35% of total cellular proteins. It was readily purified to 90–95% by nickel chelation and most of the contaminants were further eliminated by anion exchange chromatography to produce 95–98% pure protein. Therefore, the protein was purified only 3-fold to reach homogeneity. The yield obtained was 5–7 mg/100 ml of culture (Table 1). The presence of the histidine tag was confirmed by Western immunoblot using an anti-histidine tag antibody (data not shown).

Results from gel filtration analysis suggest that WbpP exists as a dimer in its native form (data not shown). No apparent monomer or higher order oligomers were detected even in the presence of 100 mM salt or at low enzyme concentration.

Example 2

Figures 3A, 3B, 3C:
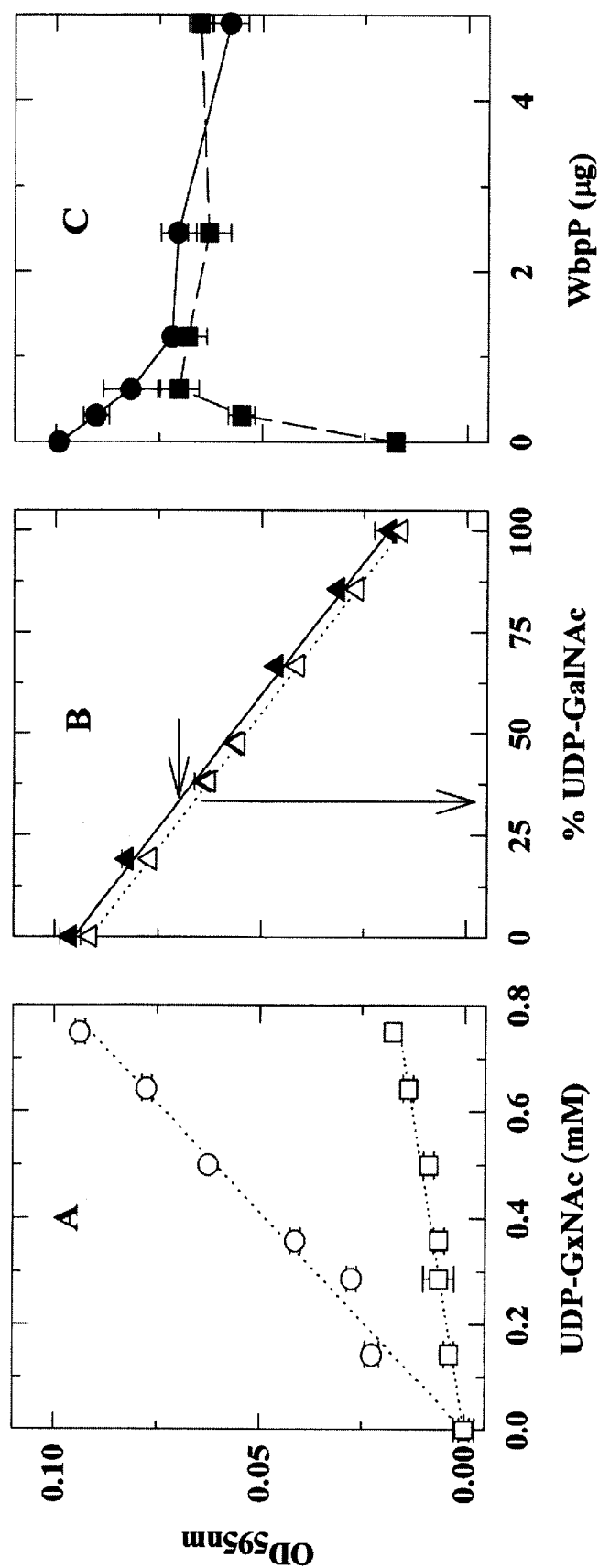
FIG. 3A is a graph showing the results of a DMAB assay using UDP-GlcNAc and UDP-GalNAc separately as standards (no enzyme reaction performed).
FIG. 3B is a graph showing the results of a DMAB assay using mixtures of UDP-GlcNAc and UDP-GalNAc and comparing with the theoretical curve obtained by calculations using standard curves (note, there was no enzyme reaction).
FIG. 3C is a graph showing the results of epimerisation of UDP-GlcNAc and UDP-GalNAc in mixtures by WbpP as a function of amount of enzyme added, using the DMAB assay.

Characteristics of the spectrophotomelric assay used for the quanfitation of GlcNAc and GalNAc—The spectrophotometric assay used to quantitate GlcNAc and GalNAc in enzymatic reactions relies on the use of DMAB which is specific for N-acetyl hexosamines. Different colorimetric yields are obtained with different N-acetyl hexosamines (REISSIG, ET AL. (1955)). For the two substrates relevant to this study, a much higher reaction yield (6 times) is obtained with GlcNAc than with GalNAc (FIG. 3A). The assay is very sensitive and allows discrimination between both substrates at low substrate concentration (0.15 mM). Moreover, the yields of reaction are additive. Hence, the composition of a mixture of GlcNAc and GalNAc obtained after enzymatic conversion can be calculated from standard curves established with each substrate separately (FIG. 3B).

Example 3

Functional characterisation of WbpP using the DMAB assay—The results obtained for WbpP using the DMAB assay are consistent with a UDP-GlcNAc C4 epimerase activity. When the enyymatic reaction was performed with UDP-GlcNAc, the total yield of the reaction with DMAB decreased (FIG. 3C). This is consistent with the formation of GalNAc that reacts poorly with DMAB. Alternatively, when the enzymatic reaction was performed with UDP-GalNAc, the yield of the reaction with DMAB increased. This is consistent with the formation GlcNAc that reacts strongly with DMAB. The activity was dependent on the quantity of enzyme added (FIG. 3C). Maximum substrate conversions obtained were approximately 30% for UDP-GlcNAc and 70% of UDP-GalNAc. Less enzyme was required to obtain maximum substrate conversion for UDP-GalNAc than for UDP-GlcNAc. The specific activity of purified WbpP was 5.6 and 2.3 Units/mg with regards to UDP-GalNAc and UDP-GlcNAc, respectively (Table 1). This represents only a 2 fold increase of the specific activity after the two-step purification procedure. This apparent low level of purification in terms of specific activity is due to the fact that the protein was expressed at very high levels since it represented 30–35% of total cellular proteins.

Example 4

Figure 4:
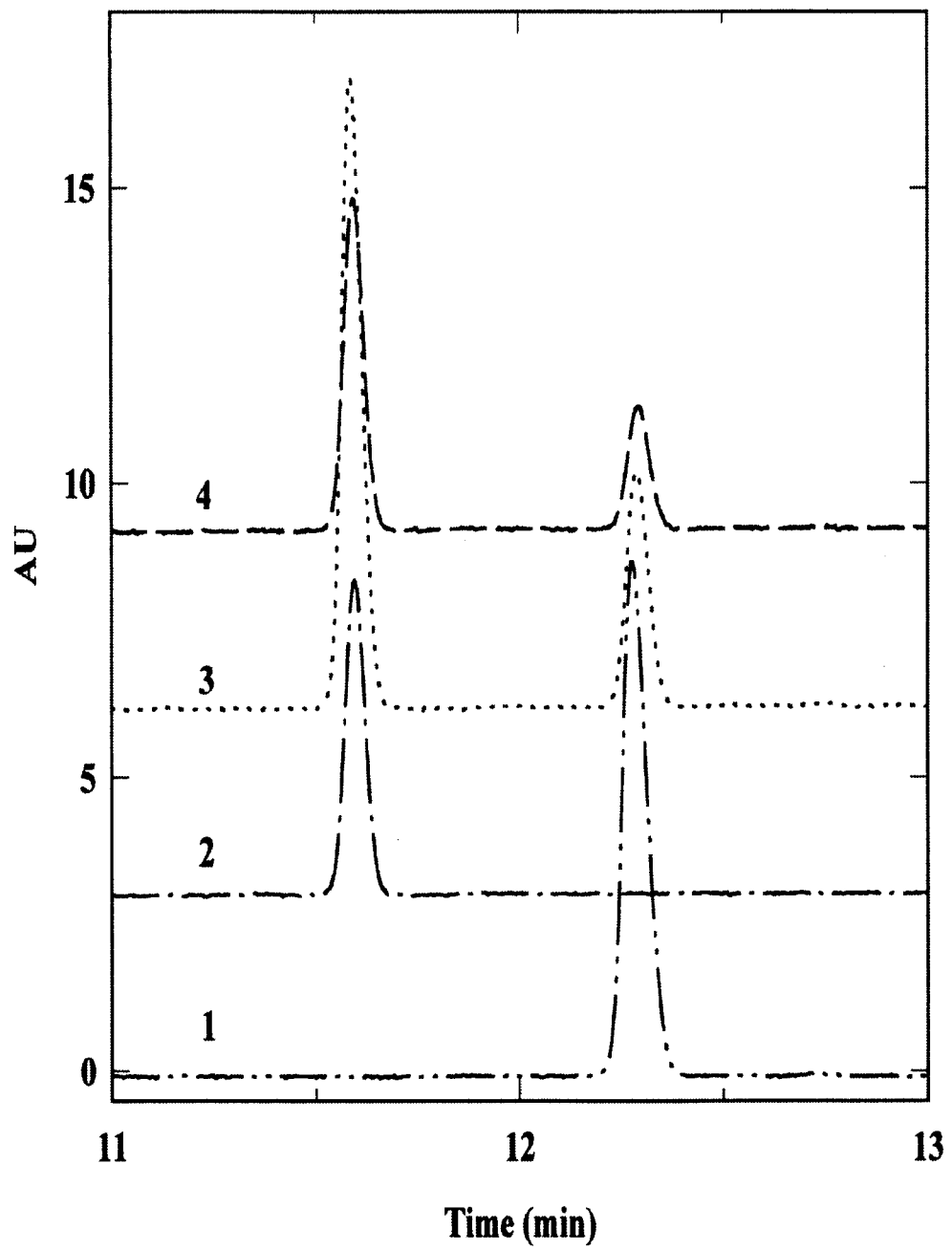
FIG. 4 is a graph showing a capillary electrophoresis analysis of the epimerisation of UDP-GlcNAc and UDP-GalNAc by WbpP at equilibrium.

Characterization of the C4 UDP-GlcNAc epimerase activity by capillary electrophoresis analysis—Capillary electrophoresis was used to confirm the identity of the reaction products after enzymatic conversion of UDP-GlcNAc or UDP-GalNAc by WbpP by comparison with standard compounds. Under analytical conditions, UDP-GlcNAc and UDP-GalNAc are well resolved, with peaks at 11.6 and 12.3 minutes, respectively. FIG. 4 shows that UDP-GlcNAc and UDP-GalNAc are interconverted into one another by WbpP, thus confirming its C4 epimerase activity on these substrates. At equilibrium, the yields of enzymatic conversion are the same as calculated from the DMAB assay data.

Example 5

Figure 5:
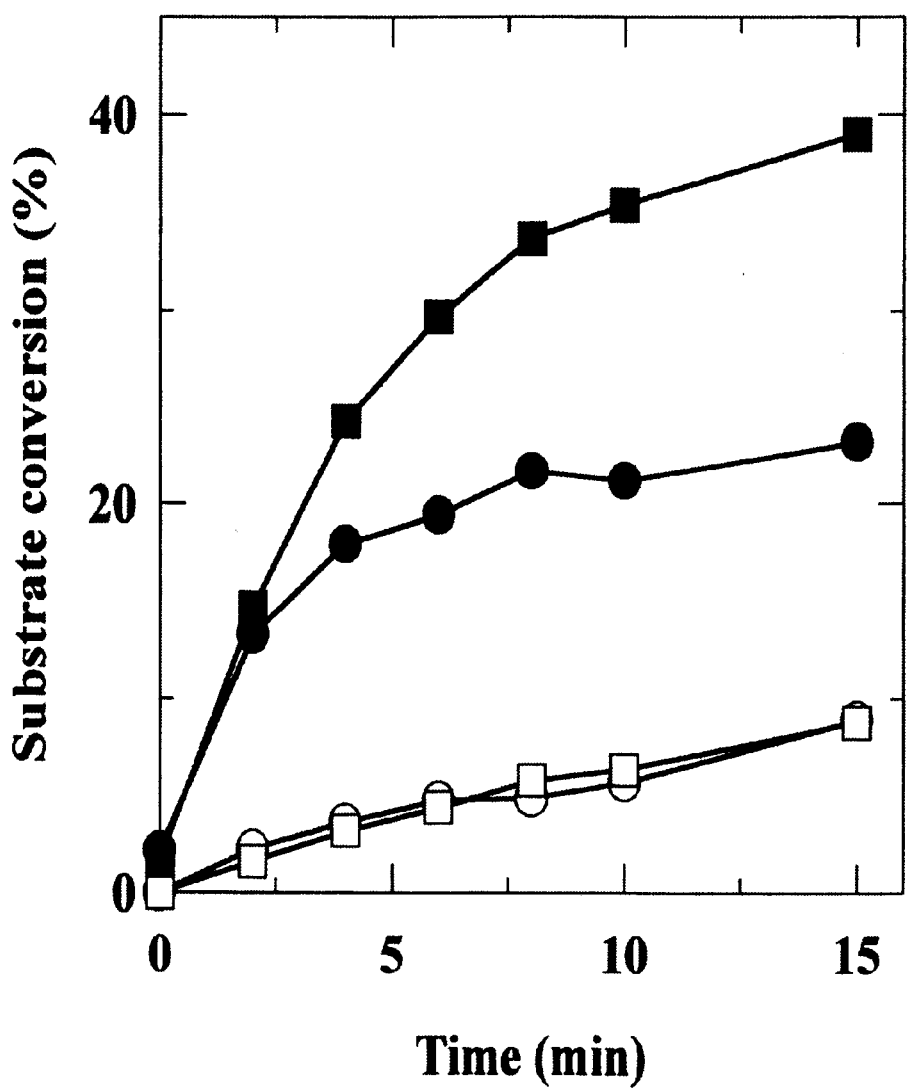
FIG. 5 is a graph showing the relationship of time course of epimerisation of UDP-GlcNAc and UDP-GalNAc by WbpP as measured by capillary electrophoresis.

Determination of the kinetic parameters for UDP-GlcNAc and UDP-GalNAc by capillary electrophoresis—Time course experiments performed with different enzyme dilutions indicate that the rate of conversion of UDP-GlcNAc is much slower than that of UDP-GalNAc at equal enzyme dilution (FIG. 5). Initial rates conditions were selected by choosing the enzyme dilutions that allow transformation of less than 10% of the substrate in 3 min, for substrates concentrations ranging from 0.02 to 1.75 mM. The Km and Vmax paramektrs of WbpP for each substrate were determined under these initial rates conditions (Table 2). The Km values derived from Eadie-Hofstee plots are 224 and 197 μM for UDP-GlcNAc and UDP-GalNAc, respectively. The enzyme shows an equal affinity for these substrates.

Example 6

Determination of the physico-chemical parameters: optimal pH, temperature and storage conditions—WbpP has a broad pH range of activity, with significant activity observed for pH>6.5 and an optimum between pH 7 and 8 (data not shown). The enzyme is also active over a wide range of temperatures (data not shown) with an optimum between 37 and 42° C. The enzyme can be kept active without any significant loss of activity when stored at −20° C. in 25% glycerol or 20% adonitol in Tris 20 mM, pH 8 (data not shown).

Example 7

Substrate specificity—A glucose-specific spectrophotometric assay relying on the use of glucose oxidase (Moreno et al. (1981)) was used to study the substrate specificity for WbpP. Using this assay, it was shown that WbpP can use UDP-Glc as a substrate (FIG. 6) but the identity of the reaction product is unknown Also, UDP-Glc was produced when the reaction was performed with UDP-Gal as a substrate. These results are consistent with a C4 epimerase activity on the non-acetylated substrates UDP-Glc and UDP-Gal. From these results, the product of UDP-Glc modification by WbpP is expected to be UDP-Gal but its identity needs to be confirmed by analytical methods. Also, the rate of conversion was significantly higher for UDP-Gal than UDP-Glc at equal enzyme dilution (FIG. 6). At equilibrium, approximately 40% of UDP-Gal were trainformed to UDP-Glc whereas only 15% of UDP-Glc were modified by the enzyme. Capillary electrophoresis analysis confirmed without ambiguity that WbpP also has C4 epimerase activity on UDP-Glc and UDP-Gal (FIG. 7) and confirmed that the maximum conversion were 40 and 17% for UDP-Gal and UDP-Glc, respectively.

Example 8

Determination of the kinetic parameters or UDP-Glc and UDP-Gal by capillary electrophoresis—The kinetic parameters determined under initial rates conditions are summarised in Table 2. The Km values are 237 and 251 μM for UDP-Glc and UDP-Gal, respectively. The Vmax values are 54 and 82 pmol/min.

Analysis of NAD+ or divalent cations requirements by capillary electrophoresis—The addition of $NAD^1$, $Mg2^1$, $Ca^{2+}$ or $Mn^{2+}$ to the reaction mixture was not necessary for the C4 epimerase activity of WbpP, would it be on the acetylated or non-acetylated forms of the substrates as determined by capillary electrophoresis (data not shown).

Extraction of NAD+/NADH from purified WbpP—Tightly bound NAD+/NADH could be extracted from highly purified and extensively dialysed WbpP after complete digestion with proteinase K. The released nucleotide was reduced to NADH by sodium borohydride treatment. A yield of 0.7 to 0.8 mol of NAD(H)/mol of WbpP was calculated from the absorbance at 340 nm (data not shown). This indicates that WbpP binds to the nucleotide tightly during its synthesis.

Discussion of Examples

UDP-GClcNAc is an essential precursor of surface carbohydrate biosynthesis (SHIBAEV (1986)), both in bacteria where it is the precursor of peptidoglycan, capsule or lipopolysaccharide biosynthesis, and in humans, where it is the main precursor involved in cell surface sialylation (KEPPLER ET AL. (1999)). Though the requirements of UDP-GlcNAc modifying enzymes such as C2- and C4-epimerases or C6 dehydratases (Keppler et al. (1999); Kiser et al. (1999); Plumbridge et al. (1999); Belanger et al. (1999); Dean et al. (1999)) has been inferred from in vivo experiments and structural analysis of various surface carbohydrates, very little information is available at the biochemical level on the enzymes responsible for such activities.

WbpP is a small protein essential for the biosynthesis of B-band LPS in *Pseudomonas aeruginosa* serotype O6 (12). Previously, the exact function of this enzyme was unknown. Sequence analysis indicated that it most likely belongs to the short chain dehydrogenase/reductase (SDR) family. The variety of enzymatic functions represented in the SDR family doesn't allow for a specific functional assignment for WbpP. Most enzymes belonging to this family share the same initial steps of catalysis resulting in the formation of a 4-hexosulose intermediate that can subsequently lead to the formation of a variety of new carbohydrates such as epimers, deoxysugars or branched carbohydrates. Hence belonging to this family is not a sufficient criteria for specific functional assignment. Comparisons of the LPS composition of organisms that exhibit WbpP or a homologue suggested that WbpP might be a C4 epimerase specific for UDP-GlcNAc. The validity of such an assignment is supported by successful complementation of a wbpP null mutant of *P. aeruginosa* by a *Salmonella typhi* homologue, wcdB. This homologue of wbpP has been shown to be involved in the biosynthesis of a homopolymer of α-1,4 2-deoxy-2-N-acetylgalactusamine uronic acid (19), However, another homologue, WbpK, showing 51% homology to WbpP is localized in the gene cluster for B-band LPS biosynthesis in *P. aeruginosa* serotype O5 (PAO1)) where its function is at present unknown. The O5 LPS contains FucNAc, which was previously proposed to arise from epimerisation of UDP-GlcNAc to UDP-GalNAc followed by dehydration and reduction to UDP-PucNAc. Hence, a UDP-GlcNAc C4 epimerase activity was also expected to exist in serotype O5. $WbpK_{O5}$ was the best candidate for such an epimerase as judged by its high level of homology to $WpbP_{O6}$. Complementation analysis using a $WbpK_{O5}$ knockout showed that $WbpP_{O6}$ is not able to rescue LPS biosynthesis in PAO1 (this study, data not shown). This suggests that $WbpP_{O6}$ and $WbpK_{O5}$ have a different function and/or substrate specificity despite their high level of sequence conservation. Hence, in addition to providing the first description of a UDP-GlcNAc C4 epimerase at the biochemical level, the characterisation of WbpP will also be useful to clarify ambiguous biosynthetic pathways for LPS biosynthesis in organisms that possess homologues of WbpP.

As mentioned above, the existence of UDP-N-acetylglucosamine 4-epimerase activity has been suggested from the analysis of the surface carbohydrates of a variety of organisms or even mammalian tissues. However, the experimental demonstration of the existence of the activity has only been reported on two occasions. The first one was the description of both UDP-GlcNAc and UDP-Glc C4 epimerase activity associated with a protein fraction isolated from porcine submaxillary gland (Piller et al. (1983)). In this study, the purified enzyme performs with equal or higher efficiency on the non-acetylated substrates than on the acetylated ones. Hence, it is doubtful that the activity arises from a genuine UDP-GlcNAc C4 epimerase but rather is a side-reaction of a standard GalL homologue. The sequence of the enzyme was not provided to resolve the question. In the second case, a UDP-N-acetylglucosamine 4-epimerase activity was linked with the gneA locus in Bacillus subtilis (Estrela et al. (1999)). Assays were performed using whole cell extracts and the enzyme was not purified. Considering that the substrate and product involved in this reaction are shared by a variety of sugar-nucleotide modifying enzymes, results obtained using whole cell extracts are not unequivocal. The biochemical characterisation described in here and performed in vitro using overexpressed and purified enzyme is the first unambiguous demonstration of the existence of a specific UDP-GlcNAc C4 epimerase and provides the first kinetic analysis of such an enzyme.

Though numerous spectrophotoinetric assays are available to study the UDP-Glc C4 epimerase activity, none is available for the UDP-GlcNAc C4 epimerase activity. Most assays rely on the coupling of the epimerisation reaction to a secondary enzymatic reaction that is usually very specific for the substrate or product in its non-acetylated form (Moreno et al. (1981); Wilson et al. (1969)). A spectrophotometric assay using p-dimethylaminobenzaldehyde (DMAB) was designed to measure C4 epimerase activity on the N-acetylated substrates, UDP-GlcNAc and UDP-GalNAc. The results obtained with the D)MAB assay as described in this study are consistent with a C4 epimerase activity involving UDP-GlcNAc and UDP-CalNAc. But other activities resulting in the production of different N-acetylhexosamines derivatives with different reactivities towards DMAB cannot be excluded. Hence, capillary electrophoresis was used to provide the proof for the identity of the reaction products. The results from CE analysis clearly confirmed that WbpP is a UDP-GlcNAc C4 epimerase.

Kinetic analysis was carried out under initial rates conditions using the standard Michaelis-Menten model. One of the assumptions of this model is that no product can be used as a substrate. The initial rates conditions used in the present examples ensured that no more than 10% of the substrate was used up by the enzyme, hence maintaining product re-conversion to a minimum. Kinetic analysis revealed that WbpP has the same affinity for UDP-GalNAc and UDP-GlcNAc but the reaction proceeds at a faster rate for the former than the latter. Moreover, the kcat shows that for an equal amount of enzyme present in the reaction, the conversion of UDP-GalNAc to UDP-GlcNAc is more efficient than the reverse reaction. This is also apparent at equilibrium where 70% of UDP-GalNAc are converted to UDP-GlcNAc whereas only 30% of UDP-GlcNAc are converted to UDP-GalNAc. Hence, in vitro, the equilibrium is shifted towards the production of UDP-GlcNAc. Such a shift of the equilibrium towards the production of the glucose isomer has been previously reported for GalE from E. coli (Wilson et al. (1969)). However, this is opposite to what is expected in vivo and in the pathway proposed for O-antigen biosynthesis in serotype O6. The use of the product by the next enzyme involved in the B-band LPIS biosynthetic pathway pulls the equilibrium towards the production of UDP-GalNAc in vivo. While not wishing to be bound to a particular theory, this could be part of a regulatory mechanism. When the biosynthesis of LPS is down-regulated as a function of varying environmental conditions (Creuzenet et al. (1999)), the UDP-GlcNAc stock is not depleted by the activity of WbpP and stays available for synthesis of other biologically important polymers such as peptidoglycan. On the other hand, the low level of UDP-GlcNAc conversion ensures that some precursors of LPS O-antigen are still present in the cell. This allows for extremely fast LPS production recovery as soon as normal environmental conditions are restored (Creuzenet et al. (1999)). Finally, the kcat/Km ratio, which is an indication of binding of the substrate to its site, suggests that the differences obtained for both substrates arc due to a less efficient binding of UDP-GlcNAc in the substrate binding pocket than of UDP-GalNAc.

The specificity of WbpP for the N-acetylated forms of the substrates was investigated. This aspect of the examples was initiated with regards to the current proposed mechanism of action for C4 epimerase GalE. The epimerase binds tightly to its substrate via the UDP moiety while the sugar moiety is more loosely bound and rotates along the bond between Pβ of UDP and O of the pyranosyl ring (Frey (1996)) while catalysis proceeds. As a result, GalE has been shown to be able to accommodate slightly different substrates, with different substitutions at positions C2 and C6 (Frey (1996); Flentke et al. (1990); Thoden et al. (1997)). It can also bind very different compounds as long as the UDP structure is preserved (Thoden et al. (1996)). In the case of WbpP, the enzyme can still perform the epimerisation of both UDP-Gal and UDP-Glc with Km values of the same order as those for the acetylated substrates. However the kcat and Vmax values clearly indicate that the catalysis is ~1000 fold less efficient with these substrates than with the acetylated ones. Moreover, the $k_{cat}$/Km ratio indicates that the binding is quite poor, especially for UDP-Glc. This is reflected by the fact that the epimerisation of the non-acetylated substrates requires the presence of significantly higher amounts of enzyme than the epimerisation of the acetylated substrates.

As observed for the acetylated substrates, the equilibrium is also shifted towards the production of UDP-Glc, but the maximum percentages of substrate conversion are much lower than in the previous case. Only 40% of UDP-Gal are converted to UDP-Glc at equilibrium, and around 12% of UDP-Glc are converted to UDP-Gal. Though WbpP can epimerise the non-acetylated substrates in vitro, the poor efficiency of catalysis and high amounts of enzyme necessary to carry such reactions indicate that these reactions are unlikely to happen in vivo and that the acetylated forms of the substrates are the preferred ones in vivo. Determination of the 3-dimensional structure and site-directed mutagenesis studies of WbpP will help decipher the molecular basis for substrate specificity in this enzyme. In P. aeruginosa, a genuine UDP-Glc C4 epimerase activity is required for the synthesis of the galactose residue found in the LPS core. Since the data show in the examples that UDP-Glc is not the preferred substrate for WbpP, this activity might be carried by a yet uncharactersised homologue of WbpP. This is consistent with the fact that inactivation of WbpP by gentamycin cassette insertion and allelic replacement does not result in the production of a truncated core in scrotype O6 (Belanger et al. (1999)). This is also consistent with the observation that Southern blotting experiments using the wbpP gene as a probe reveal the existence of homologues in all 20 serotyper of P. aeruginosa which share common core structural motifs.

Overall, the Km determined for WbpP and its different substrates are within the range of values reported in the literature for GalE epimerascs from different sources (Moreno et al. (1981); Piller et al. (1983); Wilson et al. (1969); Swanson et al. (1993); Quimby et al. (1997)).

For both series of substrates, the enzyme is active without requiring addition of exogenous $NAD^+$ or divalent cations such as $Mg^{2+}$, $Mn^{2+}$ or $Ca^{2+}$. However, the mechanism of C4 epimerisation implies the participation of a $NAD^+$ molecule as an essential coenzyme (Frey (1996)). This molecule is predicted to be bound in the Rossman fold delineated by the alternating α helix and β sheet structures and the G-x-x-G-x-x-G motif at the N-terminus of the protein. The binding site has been mapped by NMR (43) and crystallography studies (Bauer et al. (1992); Thoden et al. (1996); Thoden et al. (1996)) in GalE from *E. coli*. In GalE, the $NAD^+$ molecule is a redox cofactor responsible for reversibly and non-stereospecifically dehydrogenating carbon 4 in the pyranosyl rings of UDP-Glc and UDP-Gal. This NAD+ molecule does not dissociate from the enzyme either in the course of catalysis or between catalytic cycles. However, an NAD+-independent epimerase that carries its function via carbon-carbon bond cleavage rather than by a simple deprotonation-reprotonation mechanism was recently described (Johnson et al. (1998)). In the case of WbpP, NAD(H) could be extracted from purified and extensively dialysed enzyme after complete proteolysis and chemical reduction. This indicates that NAD(H) is present and tightly bound to the enzyme as it is expressed in *E. coli*. This molecule of NAD(H) might be recycled internally without being released into the external medium as has been proposed for GalE. Structure determination of WbpP will confirm the presence of a bound NAD+ molecule in WbpP and allow the mapping of its binding site.

Most SDR enzymes exist as dimers or tetramers in their native state (Jornvall et al. (1995)). Our gel filtration data suggest that WbpP also forms a dimer. However, contrary to what has been previously described for a UDP-GlcNAc C2 epimerase (Morgan et al. (1997)), no allosteric behaviour was observed for WbpP.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Purification table for Wbpl' established using the DMAB assay and either UDP-GlcNAc or UDP-GalNAc as a substrate[1]

| Fraction | Vol. (ml) | Conc[2] (g/l) | Protein (mg) | Yield (%) | Substrate | Total units[3] | Specific activity (U/mg) | Fold-Purif. (x) |
|---|---|---|---|---|---|---|---|---|
| Total cell extract[1] | 10 | 5.2 | 52 | 100 | UDP-GlcNAc | 11[1] | 0.2 | |
| | | | | | UDP-GalNAc | 133 | 2.6 | 1 |
| Soluble fraction[1] | 10 | 3.3 | 33 | 64 | UDP-GlcNAc | 35 | 1.1 | 1 |
| | | | | | UDP-GalNAc | 113 | 3.4 | 1.3 |
| IMAC | 3.5 | 2.8 | 9.7 | 19 | UDP-GlcNAc | 19 | 2.0 | 1.8 |
| | | | | | UDP-GalNAc | 45 | 4.6 | 1.8 |
| Anion exchange | 5 | 1.2 | 5.8 | 11 | UDP-GlcNAc | 13 | 2.3 | 2.1 |
| | | | | | UDP-GalNAc | 33 | 5.6 | 2.2 |

[1] Total cell extracts produce a high background of UDP-GlcNAc-modifying activity (9.5 units), mostly associated with the membrane fraction. In addition, the preferred direction of the reaction with WbpP is towards UDP-GlcNAc production (see kinetic data). Hence, very little difference is observed on total cell extracts expressing WbpP (20.5 units) or not (9.5 units) when reactions are performed with UDP-GlcNAc as a substrate. Therefore, the controls for analysis of total cell extracts or soluble fraction containing WbpP were total cell extract or soluble fraction of the same *E. coli* strain used for expression of WbpP but harbouring the empty pET23 vector only. Also, for UDP-GlcNAc, the reference used for the purification is the specific activity obtained with the soluble extract only, when unspecific UDP-GlcNAc modification was not observed.
[2] Conc. refers to the total protein concentration of the fraction tested for activity.
[3] One unit is defined as the amount of enzyme that allows conversion of 1 μmol of substrate in 1 min under our experimental conditions. The reactions were performed using 8.8 μl of enzyme fraction or cell extract and 0.75 mM of substrate in a total volume of 44 μl. The activity was determined using the DMAB assay.

TABLE 2

Kinetic parameters for WbpP and its four substrates as determined by capillary electrophoresis.

| Substrate | Km (μM) | Vmax (pmol/min) | Enzyme (pmol) | kcal (min$^{-1}$) | kcat/Km (mM$^{-1}$ × min$^{-1}$) |
|---|---|---|---|---|---|
| UDP-GalNAc[a] | 197 ± 15 | 840 ± 25 | 3.1 | 271 ± 7 | 1375 ± 143 |
| UDP-GlcNAc[a] | 224 ± 17 | 741 ± 22 | 6.2 | 120 ± 3 | 536 ± 57 |

TABLE 2-continued

Kinetic parameters for WbpP and its four substrates as determined by capillary electrophoresis.

| Substrate | Km ($\mu$M) | Vmax (pmol/min) | Enzyme (pmol) | kcal (min$^{-1}$) | kcat/Km (mM$^{-1}$ × min$^{-1}$) |
|---|---|---|---|---|---|
| UDP-Gal[b] | 251 ± 16 | 82 ± 3 | 436 | 0.188 ± 0.007 | 0.749 ± 0.06 |
| UDP-Glc[b] | 237 ± 53 | 54 ± 6 | 436 | 0.124 ± 0.014 | 0.523 ± 0.18 |

[a]Three independent experiments were performed where the range of substrate concentrations was shifted towards lower concentrations and the enzyme used at higher dilutions to refine the value of the parameters obtained. The results presented in this table are the results of the last experiment.
[b]Two independent experiment were performed and analysis using the spectrophotometric assay to get an estimation of the Km and V$_{max}$ parameters. A third experiment was performed with a wider substrate concentration range including 5 points below the estimated Km to refine the values of the parameters. Very similar kinetic parameters were obtained in the three experiments, but the error was considerably lower using CE data. Therefore, the results presented in this table are the results of the last experiment which were obtained by CE analysis.

FULL CITATIONS FOR REFERENCES REFERRED TO IN THE SPECIFICATION

Bauer, A. J., Rayment, I., Frey, P. A., and Holden, H. M. (1992) *Proteins* 12, 372–381.

Belanger, M., Burrows, L. L., and Lam, J. S. (1999) *Microbiology* 145, 3505–3521.

Burrows, L. L., Charter, D. F., and Lam, J. S. (1996) *Mol. Microbiol.* 22,481–495.

Creuzenet, C., Smith, M., and Lam, J. S. (1999) Pseudomonas'99: biotechnology and pathogenesis. Abstract # 93. Maui, Hi.

Cryz, S. J., Jr., Pitt, T. L., Furer, E., and Germanier, R. (1984) *Infect. Immun.* 44, 508–513.

Dean, C. R., Franklund, C. V., Retief, J. D., Coyne, M. J., Jr., Hatano, K., Evans, D. J., Pier, G. B., and Goldberg, J. B. (1999) *J. Bacteriol.* 181, 4275–4284.

Engles, W., Endert, J., Kamps, M. A. F., and Vanboven C. P. A. (1985) *Infect. Immun.* 49, 182–189.

Estrela, A. J., Pooley, H. M., de Lencastre, H., and Karamata, D. (1991) *J. Gen. Microbiol.* 137, 943–950.

Flentke, G. R., and Frey, P. A. (1990) *Biochemistry* 29, 2430–2436.

Frey, P. A. (1996) *Faseb J.* 10, 461–470.

Goldberg, J. B., and Pier, G. B. (1996) *Trends Microbiol.* 4, 490–494.

Hancock, R. E., Mutharia, L. M., Chan, L., Darveau, R. P., Speert, D. P., and Pier, G. B. (1983) *Infect. Immun.* 42, 170–177.

Johnson, A. E., and Tanner, M. E. (1998) *Biochemistry* 37, 5746–5754.

Jornvall, H., Persson, B., Krook, M., Atrian, S., Gonzalez-Duarte, R., Jeffery, J., and Ghosh, D. (1995) *Biochemistry* 34, 6003–6013.

Jornvall, H. (1999) *Adv. Exp. Med. Biol.* 463, 359–364.

Jornvall, H., Hoog, J. O., and Persson, B. (1999) *FEBS Lett.* 445, 261–264.

Keppler, O. T., Hinderlich, S., Langner, J., Schwartz-Albiez, R., Reutter, W., and Pawlita, M. (1999) *Science* 284, 1372–1376.

Kisser, K. B., Bhasin, N., Deng, L., and Lee, J. C. (1999) *J. Bacteriol.* 181, 4818–4824.

Knirel, Y. A., Vinogradov, E. V., Shashkov, A. S., Dmitriev, B. A.,

Kochetkov, N. K., Stanislavsky, E. S., and Mashilova, G. M. (1985) *Eur. J. Biochem.* 150, 541–550.

Knirel, Y. A. (1990) *Crit. Rev. Microbiol.* 17, 273–304.

Knirel, Y. A., and Kochetkov, N. K. (1994) *Biokhimiia* 59, 1784–1851.

Kochetkov, N. K., and Shibaev, V. N. (1973) *Adv. Carbohydr. Chem. Biochem.* 28, 307–399.

Konopka, J. M., Halkides, C. J., Vanhooke, J. L., Gorenstein, D. G., and Frey, P. A. (1989) *Biochemistry* 28, 2645–2654.

Marolda, C. L., and Valvano, M. A. (1995) *J. Bacteriol.* 177, 5539–5546.

Moreno, F., Rodicio, R., and Herrero, P. (1981) *Cell. Mol. Biol.* 27, 589–592.

Morgan, P. M., Sla R. F., and Tanner, M. E. (1997) *J. Am. Chem. Soc.* 119, 10269–10277.

Newton, D. T., and Mangroo, D. (1999) *Biochem. J.* 339, 63–69.

Pier, G. B., and Thomas D. M. (1982) *J. Infect. Dis.* 148, 217–223.

Piller, F., Hanlon, M. H., and Hill, R. L. (1983) *J. Biol. Chem.* 258, 10774–10778.

Pitt, T. L. (1989) *Antibiot. Chemother.* 42, 1–7.

Plumbridge, J., and Vimr, E. (1999) *J. Bacterol.* 181, 47–54.

Poole., K., Krebes, K., McNally, C., and Neshat, S. (1993) *J. Bacteriol.* 175, 7363–7372.

Poole, K., Gotoh, N., Tsujimoto, H., Zhao, Q., Wada, A., Yamasaki, T., Neshat, S., Yamagshi, J., Li, X. Z., and Nishino, T. (1996) *Mol. Microbiol.* 21, 713–724.

Quimby, B. B., Alano, A., Almashianu, S., DeSandro, A. M., Cowan, T. M., and Fridovich-Keil, J. L. (1997) *Am. J. Hum. Genet.* 61, 590–598.

Reissig, J. L. Strominger J. L., and Leloir, L. F. (1955) *J. Biol. Chem.* 217, 959–966.

Rocchetta, H. L., Burrows, L. L., and Lam, J. S (1999) *Microbiol. Mol. Biol. Rev.* 63, 523–553.

Rossmann, M. G., and Argos, P. (1975) *J. Biol. Chem.* 250, 7525–7532.

Schiller, N. L., and Hatch, R. A. (1983) *Diagn. Microbiol. Infect. Dis.* 1, 145–157.

Shibaev, V. N. (1986) *Adv. Carbohydr. Chem. Biochem.* 44, 277–339.

Srikumar, R., Tsang, E., and Poole, K. (1999) *J. Antimicrob. Chemother.* 44, 537–540.

Swanson, B. A., and Frey, P. A. (1993) *Biochemistry* 32, 13231–13236.

Thoden, J. B., Frey, P. A., and Holden, H. M. (1996) *Biochemistry* 35, 5137–5144.

Thoden, J. B., Frey, P. A., and Holden, H. M. (1996) *Biochemistry* 35, 2557–2566.

Thoden, J. B., Frey, P. A., and Holden, H. M. (1996) *Protein Sci.* 5, 2149–2163.

Thoden, J. B., Hegeman, A. D., Wesenberg, G., Chapeau, M. C., Frey, P. A., and Holden, H. M. (1997) *Biochemistry* 36, 6294–6304.

Virlogeux, I, Waxin, H., Ecobichon, C., and Popoff, M. Y. (1995) *Microbiology* 141, 3039–3047.

Wilson, D. B., and Hogness, D. S. (1969) *J. Biol. Chem.* 244, 2132–2136.

Detailed Legends for Various Figures

FIG. 1: Comparison of the primary and secondary structural features of 3 members of the short-chain dehydrogenase/reductase family: WbpP from *P. aeruginosa* serotype O6, the C4 UDP-Glc epirnerase GalE from *E. coli* and the dTDP-glucose 4,6-dehydratase RFFG from *E. coli* +, identical amino acids; *, homologous amino acids; green letters, β=sheets; pink letters, α-helices. The conserved catalytic triad is highlighted in blue. The G-X-X-G-X-X-C signature for NAD(P)+ binding proteins is highlighted in bold. Secondary structure predictions were made using the Expasy molecular biology sofware (expasy.hcuge.ch).

FIG. 2: SDS-PAGE analysis of WbpP along its purification. 30 μl aliquotes were withdrawn at each step of the purification described in the experimental section and loaded on a 10% SDS-PAGE gel. The detection was performed with Coomassie Blue staining. WbpP eluted from the anion exchange (AE) column was loaded in two lanes in different amounts to show purity and size. MW: molecular weight markers.

FIG. 3: Study of the epimerisation of UDP-GlcNAc and UDP-GalNAc by WbpP using the DMAB assay. Panel A, standard curves obtained with each compound separately. Open circles, UDP-GlcNAc; Open squares, UDP-GalNAc. Panel B, comparison of the experimental data (closed triangles) obtained for mixtures of UDP-GalNAc and UDP-GlcNAc of different proportions (constant total sugar-nucleotide concentration of 0.75 mM) and the theoretical data (open triangles) calculated from the standard curves from panel 3A. 3C: Activity of WbpP as a function of the amount of enzyme added. The reactions were performed with 0.75 nM substrate in a total volume of 35 μl for 8 min at 37° C. Closed circles, UDP-GlcNAc; Closed squares, UDP-GalNAc.

FIG. 4: Capillary electrophoresis analysis of the epimerisation of UDP-GlcNAc and UDP-GalNAc by WbpP at equilibrium. The reactions were performed in a total volume of 35 μl with 1.5 mM substrate and 17 μg of enzyme. They were incubated at 37° C. for 2 h. 1, UDP-GalNAc alone; 2, UDP-GlcNAc alone; 3, UDP-GlaNAc+WbpP; 4, UDP-GlcNAc+WbpP.

FIG. 5: Time Course of epimerisation of UDP-GlcNAc and UDP-GalNAc by WbpP as measured by capillary electrophoresis. Reactions were performed at 37° C. in 20 mM Tris pH 8 with a total reaction volume of 44 μl. The amount of purified enzyme added was 234 ng and 117 ng for reaction with UDP-GlcNAc and UDP-GalNAc, respectively. Closed circles, UDP-GlcNAc 0.075 mM; Closed squares, UDP-GalNAc 0.075 mM; Open circles, UDP-GlcNAc 1.75 mM; Open squares, UDP-GalNAc 1.75 mM.

FIG. 6: Determination of the optimum pH and temperature for the epimerisation of UDP-GlcNAc by WbpP using the DMAB assay: For the pH study (panel A), the reactions were performed with 5 mM UDP-GlcNAc and 39 ng of enzyme in a total volume of 44 μl and incubated for 10 min at 37° C. The pH between 5 and 7 were obtained with 50 mM sodium acetate buffer (open circles), whereas pH 7 to 10 were obtained with 50 mM Tris-HCl (closed circles). For the temperature study (panel B), the reactions were performed in 50 mM Tris-HCl pH 8 with 5 mM UDP-GlcNAc and 0.78 ng of enzyme in a total volume of 44 μl and 30 min incubation. For both panels, two enzymatic reactions were set up in each experimental condition and two determinations of residual UDP-GlcNAc were made per reaction. Each point represents the average of the four determinations.

Figure 7:
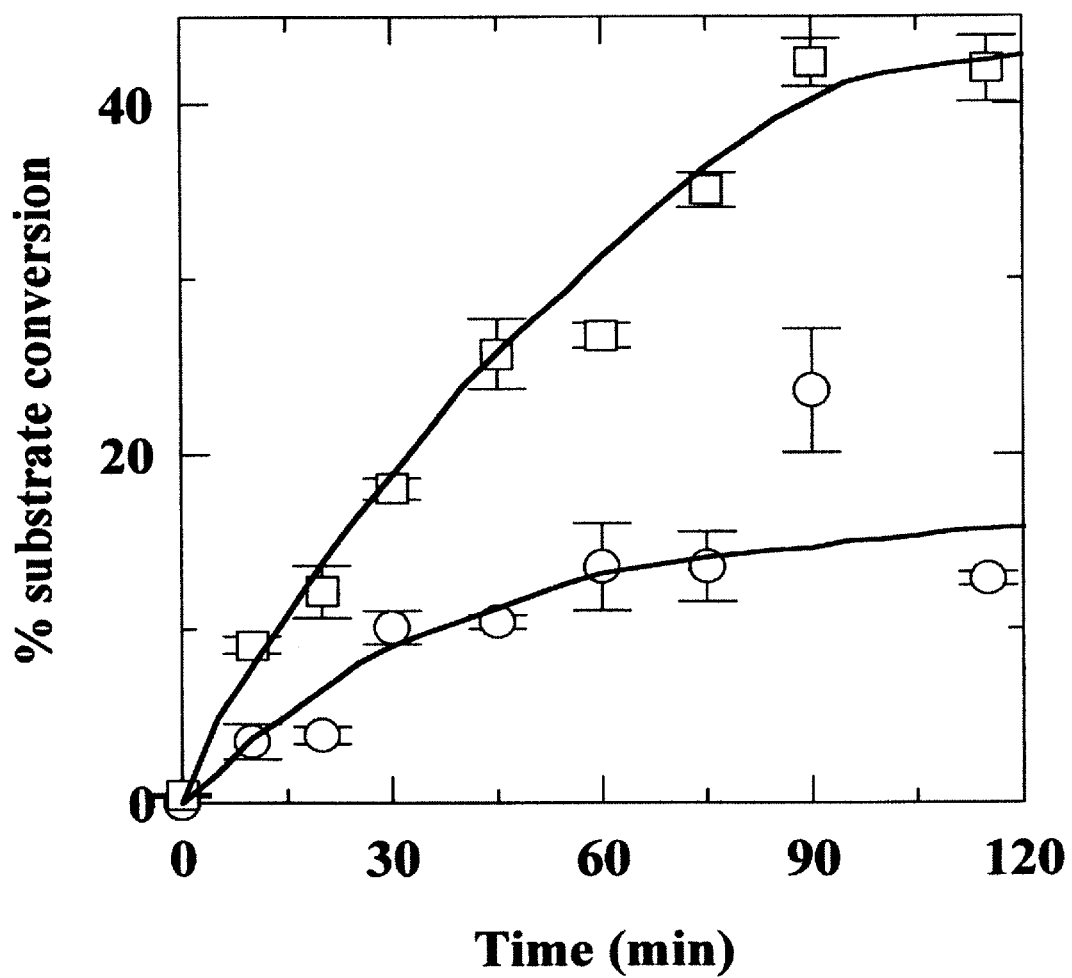
FIG. 7 is a graph illustrating the time-course for the epimerisation of UDP-Glc and UDP-Gal by WbpP using the glucose oxidas-coupled assay.

FIG. 7: Time-course for the epimerisation of UDP-Glc and UDP-Gal by WbpP using the glucose oxidase—coupled assay. Two measurements were made per time point on the same enzymatic reaction. The reactions were made with 33 μg of enzyme and 0.45 mM substrate in a total volume of 44 μl. Squares, UDP-Gal; Circles, UDP-Glc. The same differences between both substrates were observed when reactions were done with different enzyme quantities (data not shown).

Figure 8:
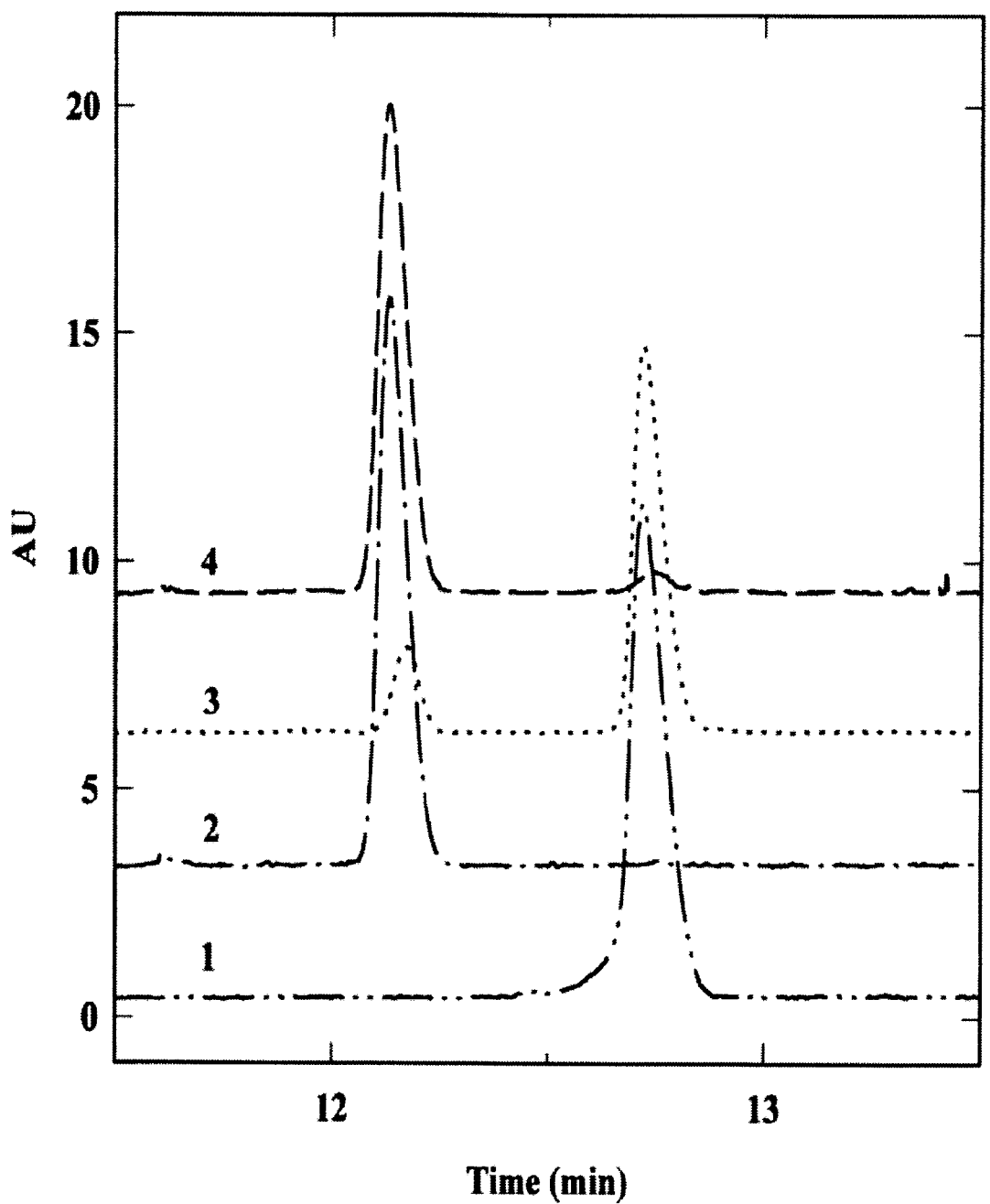
FIG. 8 is a graph showing a capillary electrophoresis analysis of the epimerisation of UDP-Glc and UDP-Gal by WbpP at equilibrium

FIG. 8: Capillary electrophoresis analysis of the epimerisation of UDP-Glc and UDP-Gal by WbpP at equilibrium. The reactions were performed in a total volume of 35 μl with 1.5 mM substrate and 17 μg of enzyme. They were incubated at 37° C. for 2 h. 1, UDP-Gal alone; 2, UDP-Glc alone; 3, UDP-Gal+WbpP; 4, UDP-Glc+WbpP.

FIG. 9. DNA sequence of WbpPO6 carrying a N-terminal hexahistidine tag (in bold). The start codon for WbpPO6 is indicated in italics. Accession number for WbpPO6: AF035937. Total number of bases: 1059.

FIG. 10 Amino acid sequence of WbpPO6 carrying a N-terminal hexahistidine lag (in bold). The start methionine of WbpPO6 is indicated in italics. Accession number for WbpPO6: AF035937. Total number of amino acids: 352.

Figure 11:
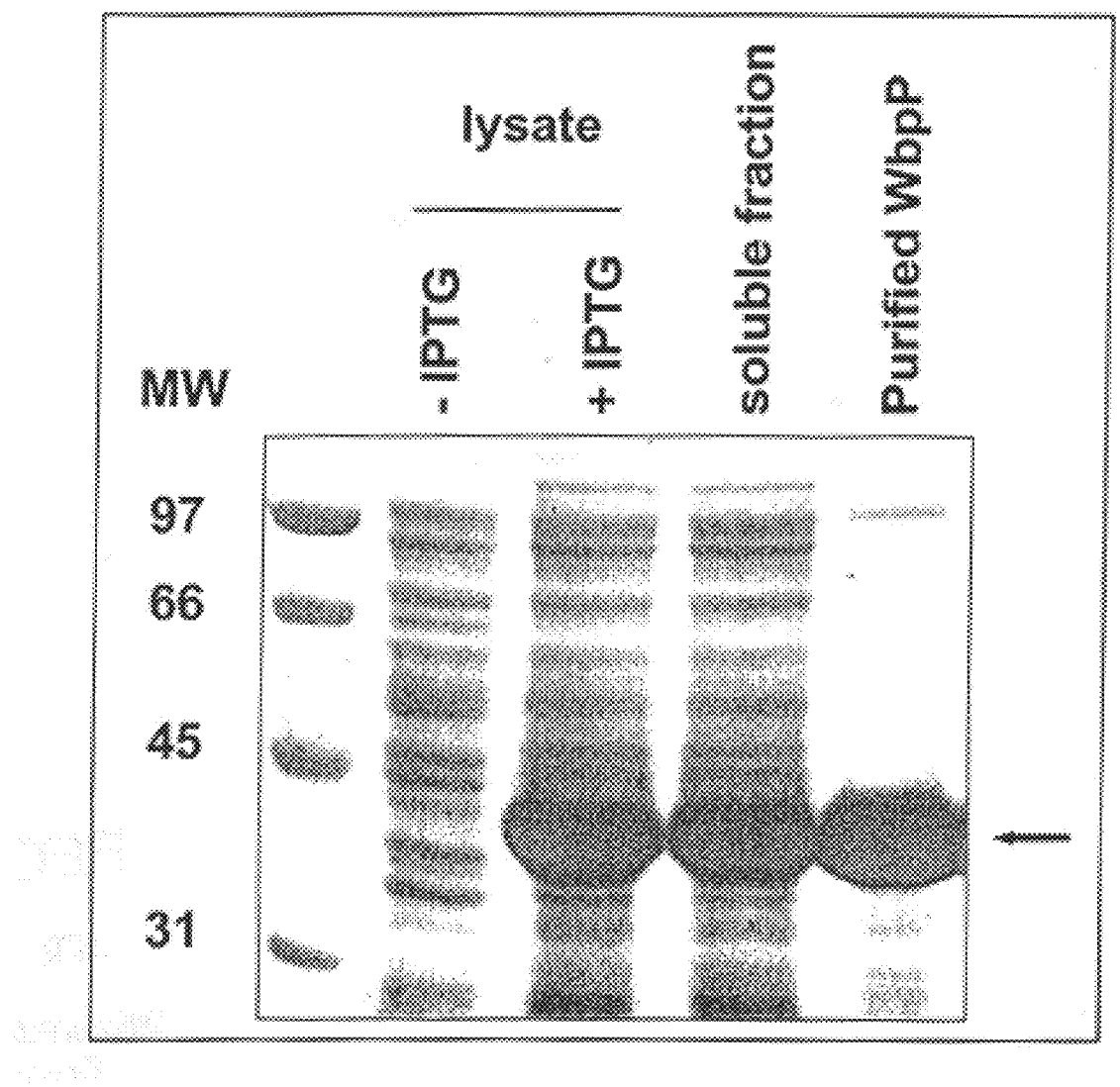
FIG. 11 is the overexpression of WbpP as a soluble protein and purification by nickel chelation.

FIG. 11. SDS-PAGE analysis of WbpP overexpressed in the pET system, in BL21DE3pLysS, under low inducer concentration (0.15 mM) and at low temperature (30° C.). The soluble fraction was purified by nickel chelation after lysis by sonication.

Figure 12:
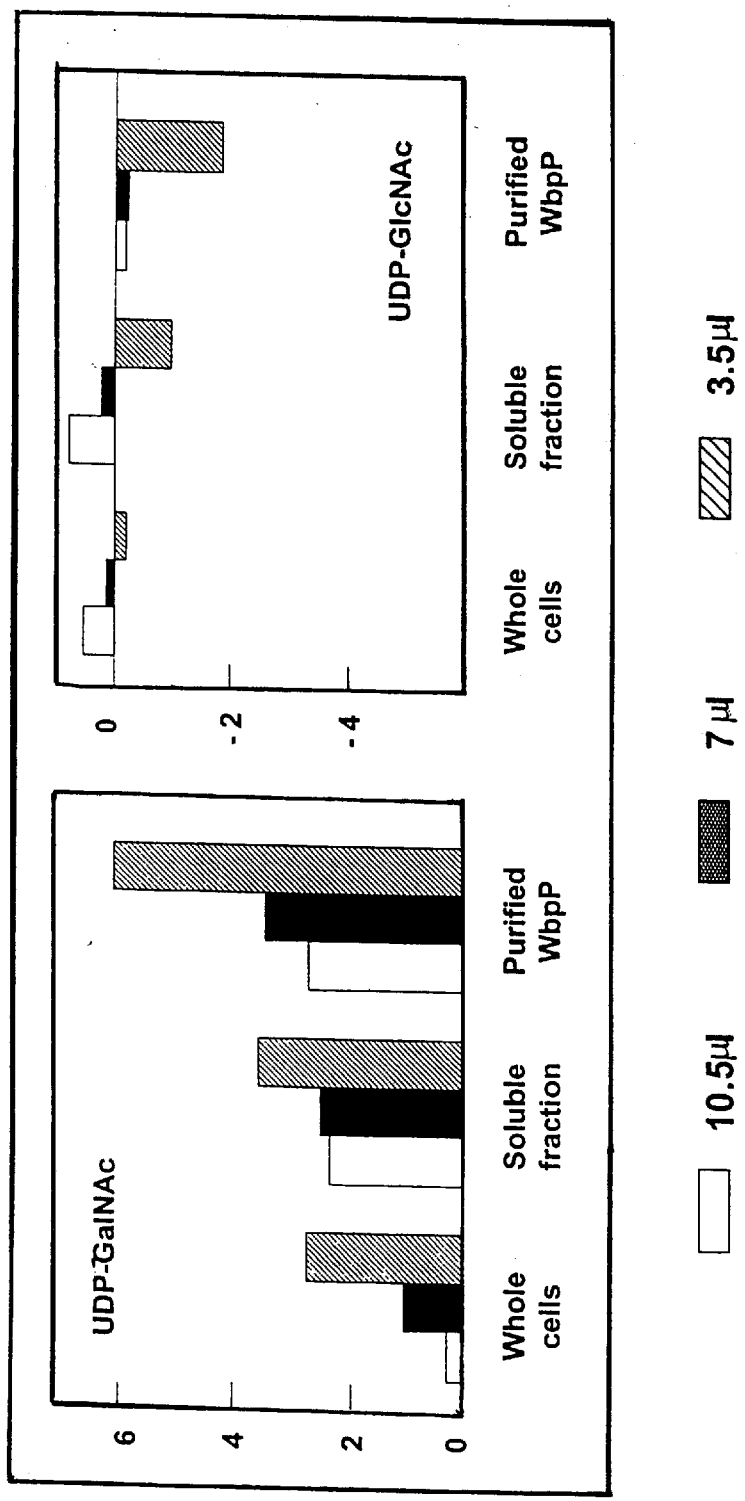
FIG. 12 shows the measurement of activity for WbpP as followed by the disappearance of different substrates (UDP-GalNAc and UDP-GlcNAc), after incubation with cell extracts containing overexpressed protein or with purified protein.

FIG. 12. Measurement of activity of WbpP as followed by the disappearance of different substrates (UDP-GalNAc and UDP-GlcNAc), after incubation with cell extracts containing overexpressed protein or with purified protein (see FIG. 14). Measurements were done in duplicates for three different quantities of proteins and normalized for the background (beg) obtained with control cell extracts or purification buffers only. The results are compatible with an interconversion of UDP-GalNAc for UDP-GlcNAc by WbpP in vitro.

We claim:

1. An isolated nucleic acid molecule comprising:
   (a) a nucleic acid sequence as shown in SEQ.ID.NO.:1, wherein T can also be U;
   (b) nucleic acid sequences fully complementary to (a); or
   (c) a nucleic acid molecule differing from any of the nucleic acids of (a) to (b) in codon sequences due to the degeneracy of the genetic code.

2. An expression vector comprising an isolated nucleic acid molecule according to claim 1.

3. A host cell transformed with an expression vector according to claim 2.

4. A method for expressing a protein encoded for by a nucleic acid molecule according to claim 1 comprising inserting a nucleic acid molecule according to claim 1 into an appropriate expression vector; transforming a host cell with the expression vector; and providing conditions which allow for expression of the protein.

5. A method according to claim 4 wherein the protein is expressed in soluble and active form.

6. A kit for detecting the presence of a nucleic acid molecule as claimed in claim 1, in a sample comprising a nucleotide probe capable of hybridizing with the nucleic acid molecule, reagents required for hybridization of the nucleotide probe with the nucleic acid molecule, and directions for its use.

* * * * *

SEQUENCE LISTING

<160> NUMBER OF SEQ ID NOS: 7

<210> SEQ ID NO 1
<211> LENGTH: 1059
<212> TYPE: DNA
<213> ORGANISM: Pseudomonas aeruginosa -continued

```
<400> SEQUENCE: 1
atgcaccacc accaccacca cggttccatg gcatgatga gtcgttatga agagctaaga      60
aaggaattgc cggcgcagcc gaaagtctgg ctgattacag gtgtggcggg ctttattggc    120
tctaatcttc ttgagacttt gctaaagctt gatcagaagg ttgtcggtct ggataatttt    180
gctactggtc atcagcggaa cctggacgaa gtgcggtcct tggttagcga gaagcaatgg    240
tcaaatttta aatttattca aggtgatatt cgcaatctgg atgattgcaa taacgcctgt    300
gcaggtgttg attacgtttt acatcaagct gccttgggtt cggtaccgcg ttctattaac    360
gatccgatca cctccaatgc aacgaacatc gatggtttct gaatatgct gattgcagcc     420
agagatgcca aggtgcagag tttcacttat gcggcaagta gctctaccta tggagatcat    480
cctggtttac cgaaggtgga ggatactata ggtaagcctc tttcccctta tgcggttacc    540
aaatatgtga tgagcttta tgccgatgtg ttttcacgct gctacggctt ttcgaccatt     600
gggcttcgtt atttcaatgt gttcggtcgt cgacaggatc ccaatggtgc ctatgcggca    660
gtcataccaa atggacctc ttcgatgatc agggtgatg acgtctatat taacggtgat      720
ggcgagacca gtcgggattt tgttatatt gaaaacaccg ttcaggccaa tctgcttgct     780
gcaaccgcgg ggcttgatgc tcgtaatcaa gtttacaata ttgctgttgg cgggcggacg    840
agtttgaatc agttgttctt tgcgcttcgc gacggccttg ccgaaaacgg tgtgtcctat    900
caccgggaac tgtttatcg tgattttagg gaggggatg tacgtcactc tctcgctgat      960
atcagcaagg ctgccaaact gctggggtat gcgccgaaat atgatgtgtc tgcaggtgtg   1020
gcgttggcca tgccttggta catcatgttt ttgaaatga                            1059

<210> SEQ ID NO 2
<211> LENGTH: 352
<212> TYPE: PRT
<213> ORGANISM: Pseudomonas aeruginosa

<400> SEQUENCE: 2

Met His His His His His His Gly Ser Met Gly Met Met Ser Arg Tyr
 1               5                   10                  15

Glu Glu Leu Arg Lys Glu Leu Pro Ala Gln Pro Lys Val Trp Leu Ile
            20                  25                  30

Thr Gly Val Ala Gly Phe Ile Gly Ser Asn Leu Leu Glu Thr Leu Leu
        35                  40                  45

Lys Leu Asp Gln Lys Val Val Gly Leu Asp Asn Phe Ala Thr Gly His
    50                  55                  60

Gln Arg Asn Leu Asp Glu Val Arg Ser Leu Val Ser Glu Lys Gln Trp
65                  70                  75                  80

Ser Asn Phe Lys Phe Ile Gln Gly Asp Ile Arg Asn Leu Asp Asp Cys
                85                  90                  95

Asn Asn Ala Cys Ala Gly Val Asp Tyr Val Leu His Gln Ala Ala Leu
            100                 105                 110

Gly Ser Val Pro Arg Ser Ile Asn Asp Pro Ile Thr Ser Asn Ala Thr
        115                 120                 125

Asn Ile Asp Gly Phe Leu Asn Met Leu Ile Ala Ala Arg Asp Ala Lys
    130                 135                 140

Val Gln Ser Phe Thr Tyr Ala Ala Ser Ser Thr Tyr Gly Asp His
145                 150                 155                 160

Pro Gly Leu Pro Lys Val Glu Asp Thr Ile Gly Lys Pro Leu Ser Pro
                165                 170                 175
```

```
Tyr Ala Val Thr Lys Tyr Val Asn Glu Leu Tyr Ala Asp Val Phe Ser
            180                 185                 190

Arg Cys Tyr Gly Phe Ser Thr Ile Gly Leu Arg Tyr Phe Asn Val Phe
            195                 200                 205

Gly Arg Arg Gln Asp Pro Asn Gly Ala Tyr Ala Val Ile Pro Lys
            210                 215                 220

Trp Thr Ser Ser Met Ile Gln Gly Asp Val Tyr Ile Asn Gly Asp
225                 230                 235                 240

Gly Glu Thr Ser Arg Asp Phe Cys Tyr Ile Glu Asn Thr Val Gln Ala
            245                 250                 255

Asn Leu Leu Ala Ala Thr Ala Gly Leu Asp Ala Arg Asn Gln Val Tyr
            260                 265                 270

Asn Ile Ala Val Gly Gly Arg Thr Ser Leu Asn Gln Leu Phe Phe Ala
            275                 280                 285

Leu Arg Asp Gly Leu Ala Glu Asn Gly Val Ser Tyr His Arg Glu Pro
            290                 295                 300

Val Tyr Arg Asp Phe Arg Glu Gly Asp Val Arg His Ser Leu Ala Asp
305                 310                 315                 320

Ile Ser Lys Ala Ala Lys Leu Leu Gly Tyr Ala Pro Lys Tyr Asp Val
            325                 330                 335

Ser Ala Gly Val Ala Leu Ala Met Pro Trp Tyr Ile Met Phe Leu Lys
            340                 345                 350

<210> SEQ ID NO 3
<211> LENGTH: 341
<212> TYPE: PRT
<213> ORGANISM: Pseudomonas aeruginosa

<400> SEQUENCE: 3

Met Met Ser Arg Tyr Glu Glu Leu Arg Lys Glu Leu Pro Ala Gln Pro
1               5                   10                  15

Lys Val Trp Leu Ile Thr Gly Val Ala Gly Phe Ile Gly Ser Asn Leu
            20                  25                  30

Leu Glu Thr Leu Leu Lys Leu Asp Gln Lys Val Val Gly Leu Asp Asn
            35                  40                  45

Phe Ala Thr Gly His Gln Arg Asn Leu Asp Glu Val Arg Ser Leu Val
        50                  55                  60

Ser Glu Lys Gln Trp Ser Asn Phe Lys Phe Ile Gln Gly Asp Ile Arg
65                  70                  75                  80

Asn Leu Asp Asp Cys Asn Asn Ala Cys Ala Gly Val Asp Tyr Val Leu
            85                  90                  95

His Gln Ala Ala Leu Gly Ser Val Pro Arg Ser Ile Asn Asp Pro Ile
            100                 105                 110

Thr Ser Asn Ala Thr Asn Ile Asp Gly Phe Leu Asn Met Leu Ile Ala
            115                 120                 125

Ala Arg Asp Ala Lys Val Gln Ser Phe Thr Tyr Ala Ala Ser Ser Ser
            130                 135                 140

Thr Tyr Gly Asp His Pro Gly Leu Pro Lys Val Glu Asp Thr Ile Gly
145                 150                 155                 160

Lys Pro Leu Ser Pro Tyr Ala Val Thr Lys Tyr Val Asn Glu Leu Tyr
            165                 170                 175

Ala Asp Val Phe Ser Arg Cys Tyr Gly Phe Ser Thr Ile Gly Leu Arg
            180                 185                 190

Tyr Phe Asn Val Phe Gly Arg Arg Gln Asp Pro Asn Gly Ala Tyr Ala
            195                 200                 205
```

-continued

Ala Val Ile Pro Lys Trp Thr Ser Ser Met Ile Gln Gly Asp Asp Val
            210                 215                 220

Tyr Ile Asn Gly Asp Gly Glu Thr Ser Arg Asp Phe Cys Tyr Ile Glu
225                 230                 235                 240

Asn Thr Val Gln Ala Asn Leu Leu Ala Ala Thr Ala Gly Leu Asp Ala
                245                 250                 255

Arg Asn Gln Val Tyr Asn Ile Ala Val Gly Gly Arg Thr Ser Leu Asn
                260                 265                 270

Gln Leu Phe Phe Ala Leu Arg Asp Gly Leu Ala Glu Asn Gly Val Ser
            275                 280                 285

Tyr His Arg Glu Pro Val Tyr Arg Asp Phe Arg Glu Gly Asp Val Arg
            290                 295                 300

His Ser Leu Ala Asp Ile Ser Lys Ala Ala Lys Leu Leu Gly Tyr Ala
305                 310                 315                 320

Pro Lys Tyr Asp Val Ser Ala Gly Val Ala Leu Ala Met Pro Trp Tyr
                325                 330                 335

Ile Met Phe Leu Lys
            340

<210> SEQ ID NO 4
<211> LENGTH: 338
<212> TYPE: PRT
<213> ORGANISM: E. Coli

<400> SEQUENCE: 4

Met Arg Val Leu Val Thr Gly Gly Ser Gly Tyr Ile Gly Ser His Thr
1               5                   10                  15

Cys Val Gln Leu Leu Gln Asn Gly His Asp Val Ile Ile Leu Asp Asn
                20                  25                  30

Leu Cys Asn Ser Lys Arg Ser Val Leu Pro Val Ile Glu Arg Leu Gly
            35                  40                  45

Gly Lys His Pro Thr Phe Val Glu Gly Asp Ile Arg Asn Glu Ala Leu
        50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
                100                 105                 110

Ala Ala Asn Val Lys Asn Phe Ile Phe Ser Ser Ser Ala Thr Val Tyr
            115                 120                 125

Gly Asp Gln Pro Lys Ile Pro Tyr Val Glu Ser Phe Pro Thr Gly Thr
        130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
                180                 185                 190

Pro Gln Gly Ile Pro Asn Asn Leu Met Pro Tyr Ile Ala Gln Val Ala
            195                 200                 205

Val Gly Arg Arg Asp Ser Leu Ala Ile Phe Gly Asn Asp Tyr Pro Thr
        210                 215                 220

Glu Asp Gly Thr Gly Val Arg Asp Tyr Ile His Val Met Asp Leu Ala
225                 230                 235                 240

```
Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270

Val Asn Ala Phe Ser Lys Ala Cys Gly Lys Pro Val Asn Tyr His Phe
        275                 280                 285

Ala Pro Arg Arg Glu Gly Asp Leu Pro Ala Tyr Trp Ala Asp Ala Ser
    290                 295                 300

Lys Ala Asp Arg Glu Leu Asn Trp Arg Val Thr Arg Thr Leu Asp Glu
305                 310                 315                 320

Met Ala Gln Asp Thr Trp His Trp Gln Ser Arg His Pro Gln Gly Tyr
                325                 330                 335

Pro Asp

<210> SEQ ID NO 5
<211> LENGTH: 355
<212> TYPE: PRT
<213> ORGANISM: E. Coli

<400> SEQUENCE: 5

Met Arg Lys Ile Leu Ile Thr Gly Gly Ala Gly Phe Ile Gly Ser Ala
1               5                   10                  15

Leu Val Arg Tyr Ile Ile Asn Glu Thr Ser Asp Ala Val Val Val
                20                  25                  30

Asp Lys Leu Thr Tyr Ala Gly Asn Leu Met Ser Leu Ala Pro Val Ala
            35                  40                  45

Gln Ser Glu Arg Phe Ala Phe Glu Lys Val Asp Ile Cys Asp Arg Ala
        50                  55                  60

Glu Leu Ala Arg Val Phe Thr Glu His Gln Pro Asp Cys Val Met His
65                  70                  75                  80

Leu Ala Ala Glu Ser His Val Asp Arg Ser Ile Asp Gly Pro Ala Ala
                85                  90                  95

Phe Ile Glu Thr Asn Ile Val Gly Thr Tyr Thr Leu Leu Glu Ala Ala
            100                 105                 110

Arg Ala Tyr Trp Asn Ala Leu Thr Glu Asp Lys Lys Ser Ala Phe Arg
        115                 120                 125

Phe His His Ile Ser Thr Asp Glu Val Tyr Gly Asp Leu His Ser Thr
130                 135                 140

Asp Asp Phe Phe Thr Glu Thr Thr Pro Tyr Ala Pro Ser Ser Pro Tyr
145                 150                 155                 160

Ser Ala Ser Lys Ala Ser Ser Asp His Leu Val Arg Ala Trp Leu Arg
                165                 170                 175

Thr Tyr Gly Leu Pro Thr Leu Ile Thr Asn Cys Ser Asn Asn Tyr Gly
            180                 185                 190

Pro Tyr His Phe Pro Glu Lys Leu Ile Pro Leu Met Ile Leu Asn Ala
        195                 200                 205

Leu Ala Gly Lys Ser Leu Pro Val Tyr Gly Asn Gly Gln Gln Ile Arg
    210                 215                 220

Asp Trp Leu Tyr Val Glu Asp His Ala Arg Ala Leu Tyr Cys Val Ala
225                 230                 235                 240

Thr Thr Gly Lys Val Gly Glu Thr Tyr Asn Ile Gly Gly His Asn Glu
                245                 250                 255

Arg Lys Asn Leu Asp Val Val Glu Thr Ile Cys Glu Leu Leu Glu Glu
            260                 265                 270
```

```
                                                  -continued

Leu Ala Pro Asn Lys Pro His Gly Val Ala His Tyr Arg Asp Leu Ile
        275                 280                 285

Thr Phe Val Ala Asp Arg Pro Gly His Asp Leu Arg Tyr Ala Ile Asp
    290                 295                 300

Ala Ser Lys Ile Ala Arg Glu Leu Gly Cys Val Pro Gln Glu Thr Phe
305                 310                 315                 320

Glu Ser Gly Met Arg Lys Thr Val Gln Trp Tyr Leu Ala Asn Glu Ser
                325                 330                 335

Trp Trp Lys Gln Val Gln Asp Gly Ser Tyr Gln Gly Glu Arg Leu Gly
            340                 345                 350

Leu Lys Gly
        355

<210> SEQ ID NO 6
<211> LENGTH: 32
<212> TYPE: DNA
<213> ORGANISM: Pseudomonas aeruginosa

<400> SEQUENCE: 6
caatgccatg ggaatgatga gtcgttatga ag                              32

<210> SEQ ID NO 7
<211> LENGTH: 30
<212> TYPE: DNA
<213> ORGANISM: Pseudomonas aeruginosa

<400> SEQUENCE: 7
ttaacgaatt ctcatttcaa aaacatgatg                                 30
```